United States Patent
Kovacs et al.

(10) Patent No.: US 8,518,715 B2
(45) Date of Patent: *Aug. 27, 2013

(54) BIFUNCTIONAL POLYAZAMACROCYCLIC CHELATING AGENTS

(75) Inventors: Zoltan Kovacs, Lewisville, TX (US); Garry E. Kiefer, Richardson, TX (US); Corinne Bensimon, Nepean (CA); A. Dean Sherry, Dallas, TX (US); Gyula Tircso, Debrecen (HU); Cara Ferreira, Surrey (CA)

(73) Assignee: Nordion (Canada) Inc., Kanata, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/476,794

(22) Filed: May 21, 2012

(65) Prior Publication Data

US 2012/0276001 A1 Nov. 1, 2012

Related U.S. Application Data

(62) Division of application No. 12/282,333, filed as application No. PCT/CA2007/000369 on Mar. 6, 2007, now Pat. No. 8,198,101.

(60) Provisional application No. 60/780,865, filed on Mar. 10, 2006.

(51) Int. Cl.
*G01N 33/532* (2006.01)
*C07D 257/00* (2006.01)
*C07D 273/00* (2006.01)

(52) U.S. Cl.
USPC ........... 436/544; 514/156; 540/474; 540/467; 540/469

(58) Field of Classification Search
None
See application file for complete search history.

(56) References Cited

U.S. PATENT DOCUMENTS

| | | | |
|---|---|---|---|
| 5,403,572 A | 4/1995 | Gries et al. | |
| 5,480,990 A | 1/1996 | Kiefer et al. | |
| 5,531,978 A | 7/1996 | Berg et al. | |
| 6,670,456 B2 | 12/2003 | Frank et al. | |
| 8,198,101 B2* | 6/2012 | Kovacs et al. | 436/544 |
| 2006/0210479 A1* | 9/2006 | Young et al. | 424/9.363 |

FOREIGN PATENT DOCUMENTS

| | | |
|---|---|---|
| EP | 232 751 | 8/1987 |
| EP | 292 689 | 11/1988 |
| JP | 5-112567 A | 5/1993 |
| JP | 2004-529763 A | 9/2004 |
| JP | 2004-532820 A | 10/2004 |
| WO | 97/40055 | 10/1997 |
| WO | 02/067999 A2 | 9/2002 |
| WO | 02/085413 A1 | 10/2002 |

OTHER PUBLICATIONS

Stimmel et al. "Yttrium-90 chelation properties of tetraazatetraacetic acid macrocycles, diethylenetriaminepentaacetic acid analogues, and a novel terpyridine acyclic chelator," Bioconjugate Chemistry, 6(2): 219-225 (1995).
Supplemental European Search Report for European Application No. 07710703.5 (mailed Mar. 7, 2011).

* cited by examiner

*Primary Examiner* — Shafiqul Haq
(74) *Attorney, Agent, or Firm* — Morgan, Lewis & Bockius LLP

(57) ABSTRACT

A bifunctional polyazamacrocyclic chelating agent of the formula (I):

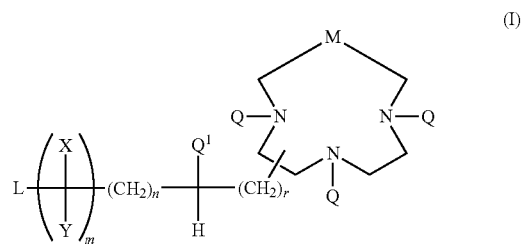

wherein:

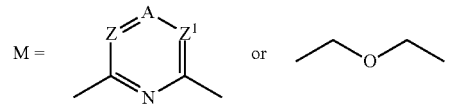

and the variables A, L, Q, $Q^1$, X, Y, Z, $Z^1$, m, n and r are as defined in the description of the present application. Also described is a complex of the above chelating agent to an ion of a metal ion, such as an ion of $^{90}Y$, $^{111}In$ or $^{177}Lu$; a conjugate of the complex covalently attached to a biological carrier; and a pharmaceutical composition containing the conjugate. A method of therapeutic treatment of a mammal involving administration of the pharmaceutical composition is also described.

15 Claims, 9 Drawing Sheets

BIFUNCTIONAL POLYAZAMACROCYCLIC CHELATING AGENTS

CROSS-REFERENCE TO RELATED APPLICATIONS

This is a divisional application of U.S. application Ser. No. 12/282,333 (filed Feb. 3, 2009), which is a U.S. National Phase Application of International Application No. PCT/CA2007/000369 (filed Mar. 6, 2007), which claims the benefit of U.S. Provisional Application No. 60/780,865 (filed Mar. 10, 2006), all of which are herein incorporated by reference in their entireties.

FIELD OF INVENTION

The present invention relates to bifunctional polyazamacrocyclic chelating agents, to complexes of these chelating agents with metal ions, and to conjugates of these complexes with a biological carrier. More particularly, the present invention relates to ligand structures that exhibit unexpectedly rapid complexation kinetics with the lanthanide series of metal ions. The resulting chelate structures are useful in nuclear medicine applications where efficient and fast metal ion incorporation is a desirable feature.

BACKGROUND OF THE INVENTION

Diagnostic imaging and therapeutic radiopharmaceuticals play an important role in modern medicine. Many of the important radionuclides used in current applications are metals positioned in the lanthanide series.[1] This family of metals possesses diversity in nuclear properties that can be harnessed for both diagnostic and therapeutic applications. In nearly all cases, these metal ions are inherently toxic in a simple salt form and must be sequestered into an organic chelating compound (ligand) in order to render them biologically compatible. Furthermore, the ligand architecture is vitally important for creating a linking group for attachment to a biological targeting molecule.

Chelating agents for the lanthanide metal ions have been the subject of intense fundamental and applied research for many years driven in part by advancements in medicine.[2] For example, the emergence of magnetic resonance imaging (MRI) as a new diagnostic modality brought with it the need for paramagnetic metal based contrast agents to enhance image quality, for this application gadolinium from the lanthanide series is preferred.[3] As a result, there has been an exponential acceleration in the design and synthesis of new ligand systems that can hold up to the rigors of in vivo applications for MRI.[4] Equally important is the fact that these same ligand systems are being recruited for other members of the lanthanide series ($^{153}$Sm, $^{177}$Lu, $^{166}$Ho, $^{90}$Y) which possess highly desirable nuclear properties making them useful in radiopharmaceutical agents.[5] The adaptability of similar ligands for all lanthanide ions is due to the very uniform and predictable properties intrinsic to the lanthanide series.

The critical prerequisites of all chelates intended for human use is that they remain stable in the body (no dissociation of the metal) and that they can be prepared reasonably fast. This latter point is more applicable to nuclear applications where isotope half-life is a critical consideration in the formulation process. Chelate stability is assessed in terms of thermodynamic and kinetic inertness. The most desirable chelates for biomedical applications are those that have the highest thermodynamic stability. However, these ligand systems usually require longer reaction times and additional energy input is needed to form the final complex.

One of the most popular ligands for both MRI and nuclear medicine has been diethylenetriamainepentaacetic acid (DTPA). DTPA is a linear ethyleneamine based chelating agent that forms thermodynamically stable complexes with the lanthanide series and displays reasonably fast kinetics of complexation. More recently the use of macrocyclic chelating agents based on 1,4,7,10-tetraazacyclododecane-1,4,7,10-tetraacetic acid (DOTA) have become increasingly important in medicine due to the improved thermodynamic stability with lanthanides relative to DTPA.[6] Nevertheless, both DTPA and DOTA have been modified for covalent attachment to biological targeting vectors and these bifunctional chelating agents (BFCA's) are now a cornerstone of the growing biotargeted radiopharmaceutical market.[7] The perceived advantage of using a DTPA-based bifunctional chelating agent is that the kinetics of complexation is faster than for DOTA and this can be a significant consideration in view of the very low number of BFCA's present on a monoclonal antibody and the necessarily dilute complexation environment. However, an increasing body of knowledge suggests that low levels of metal do indeed dissociate in vivo from DTPA targeted conjugates which can be a serious consideration. Conversely, this type of toxicity issue is circumvented by employing a DOTA-based BFCA however the slow kinetics of complexation remains an issue to be addressed.

It would be advantageous to develop a bifunctional chelating agent (BFCA) that combined the rapid complexation kinetics of DTPA and the superior thermodynamic in vivo stability displayed by DOTA.[8] A novel BFC possessing these desirable features would find broad utility in the radiopharmaceutical industry and furnish an unmet need in any application where fast complexation and long term stability is a requirement.

Numerous tetraazamacrocyclic ligand systems have been reported in the literatue and shown to possess similar complexation properties as observed for related DOTA-type ligands. For example, U.S. Pat. Nos. 6,670,456 and 5,403,572 disclose generic molecules having a polyazabicyclic core and a linking group having a terminal functional group capable of forming a bond with a biomolecule connected to the backbone of the polyazabicyclic core, and an optional functionalised cyclic aliphatic or aromatic group connected through one of the nitrogen atoms of the polyazabicyclic core, which is also capable of forming a bond with the biomolecule. In these reports DOTA-type ligand systems are documented as being the gold standard for biological applications which require high thermodynamic and kinetic stability. Up to this point, examples of ligand systems capable of surpassing the performance of DOTA has been lacking.

SUMMARY OF THE INVENTION

The present invention relates to bifunctional polyazamacrocyclic chelating agents, to complexes of these chelating agents with metal ions, and to conjugates of these complexes with a biological carrier. More particularly, the present invention relates to ligand structures that exhibit unexpectedly rapid complexation kinetics with the lanthanide series of metal ions. The resulting chelate structures are useful in nuclear medicine applications where efficient and fast metal ion incorporation is a desirable feature.

The present invention provides a bifunctional polyazamacrocyclic chelating agent of the formula (I):

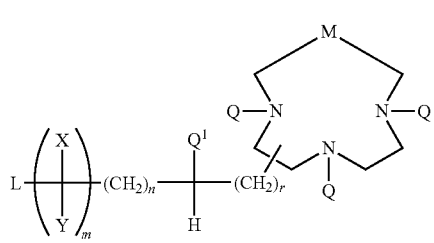
(I)

wherein:

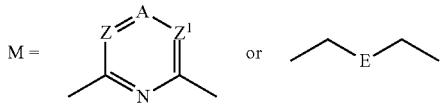

each Q is independently $(CHR^5)_pCO_2R$ or $(CHR^5)_p PO_3R^6R^7$;

$Q^1$ is hydrogen, $(CHR^5)_wCO_2R$ or $(CHR^5)_wPO_3R^6R^7$;

each R is independently hydrogen, benzyl or $C_1$-$C_4$ alkyl;

$R^6$ and $R^7$ are independently H, $C_1$-$C_6$ alkyl or ($C_1$-$C_2$ alkyl)phenyl;

each $R^5$ is independently hydrogen; $C_1$-$C_4$ alkyl or ($C_1$-$C_2$ alkyl)phenyl;

A is CH, N, C—Br, C—Cl, C—$SO_3H$, C—$OR^8$, C—$OR_9$, $N^+$—$R^{10}X^-$, or

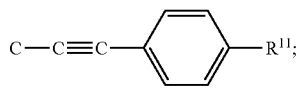

Z and $Z^1$ independently are CH, N, C—$SO_3H$, C—$CH_2$—$OR^8$ or C—C(O)—$R^{11}$;

E is O, S or P;

$R^8$ is H, $C^1$-$C^5$ alkyl, benzyl, or benzyl substituted with at least one $R^{12}$;

$R^9$ is $C_1$-$C_{16}$ alkylamino;

$R^{10}$ is $C_1$-$C_{16}$ alkyl, benzyl, or benzyl substituted with at least one $R^{12}$;

$R^{11}$ is —O—($C_1$-$C_3$ alkyl), OH or NHR—;

$R^{12}$ is H, $NO_2$, $NH_2$, isothiocyanato, semicarbazido, thiosemicarbazido, maleimido, bromoacetamido or carboxyl;

X and Y are each independently hydrogen or may be taken with an adjacent X and Y to form an additional carbon-carbon bond;

n is 0 or 1;

m is an integer from 0 to 10 inclusive;

p is 1 or 2;

r is 0 or 1;

w is 0 or 1;

L is a linker/spacer group covalently bonded to, and replaces one hydrogen atom of one of the carbon atoms to which it is joined, said linker/spacer group being represented by the formula:

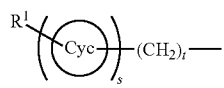

wherein:

s is an integer of 0 or 1;

t is an integer of 0 to 20 inclusive;

$R^1$ is H or an electrophilic or nucleophilic moiety which allows for covalent attachment to a biological carrier, or synthetic linker which can be attached to a biological carrier, or precursor thereof; and Cyc represents a cyclic aliphatic moiety, aromatic moiety, aliphatic heterocyclic moiety, or aromatic heterocyclic moiety, each of said moieties optionally substituted with one or more groups which do not interfere with binding to a biological carrier;

or a pharmaceutically acceptable salt thereof.

Examples of the bifunctional polyazamacrocyclic chelating agent of formula (I) include chelating agents of the formulas (II) to (V):

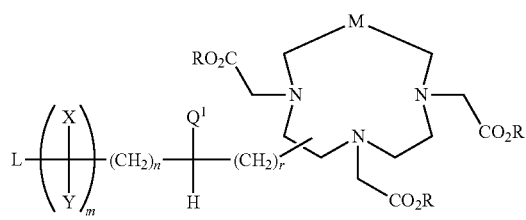
(II)

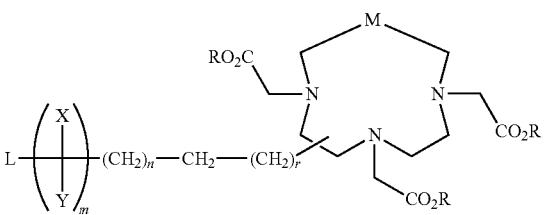
(III)

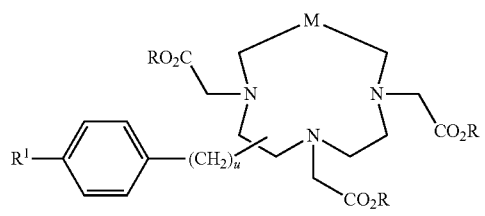
(IV)

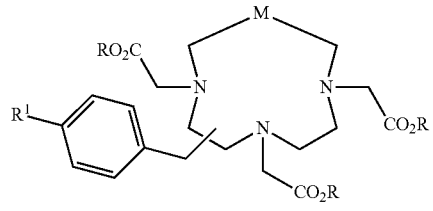
(V)

wherein the variables M, R, L, X, Y, $R^1$, m, n and r are as defined above, and u is 0, 1, 2, 3, 4 or 5.

More specifically, the present invention provides a bifunctional polyazamacrocyclic chelating agent of the of the formula (VI):

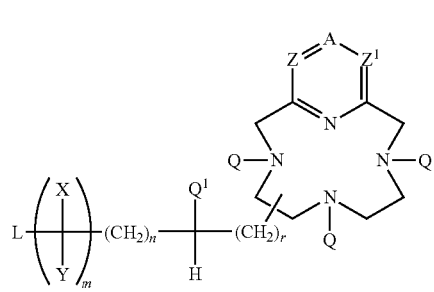
(VI)

wherein the variables A, Z, $Z^1$, L, X, Y, Q, $Q^1$, m, n and r are as defined above.

Examples of the bifunctional polyazamacrocyclic chelating agent of formula (VI) include chelating agents of the formulas (VIa) to (VIf):

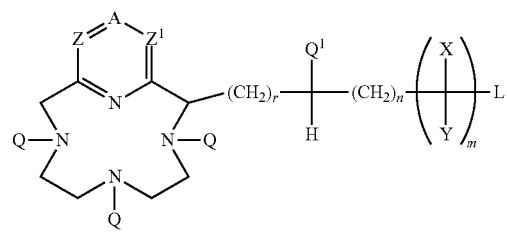
(VIa)

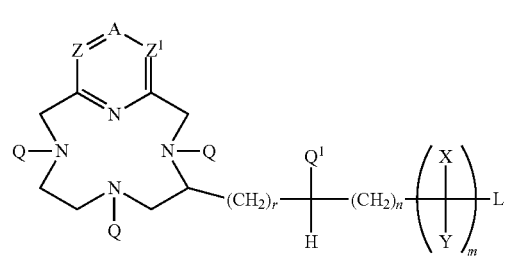
(VIb)

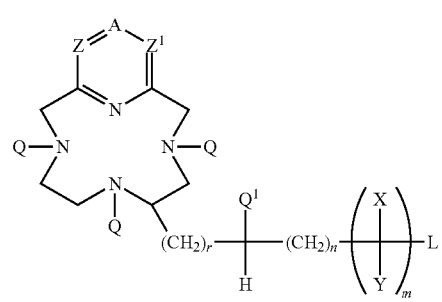
(VIc)

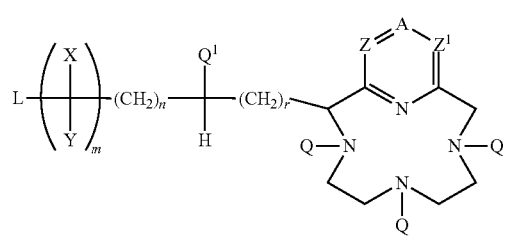
(VId)

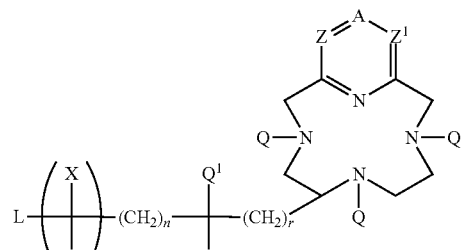
(VIe)

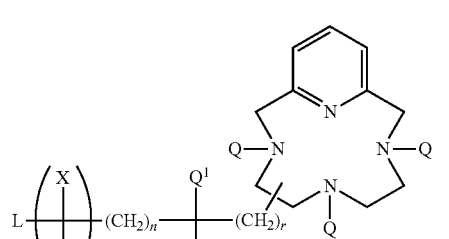
(VIf)

wherein the variables A, Z, $Z^1$, L, X, Y, Q, $Q^1$, m, n and r are as defined above.

The present invention also pertains to a bifunctional polyazamacrocyclic chelating agent of the formula (VII):

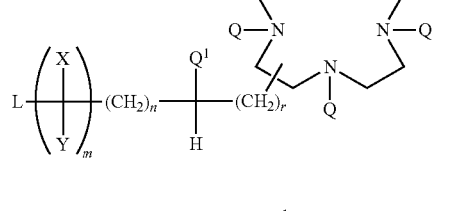
(VII)

wherein the variables L, X, Y, Q, $Q^1$, m, n and r are as defined above.

Examples of the bifunctional polyazamacrocyclic chelating agent of formula (VII) include chelating agents of the of the formulas (VIIa) to (VIIc):

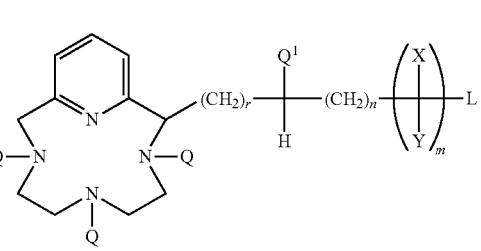
(VIIa)

(VIIb)

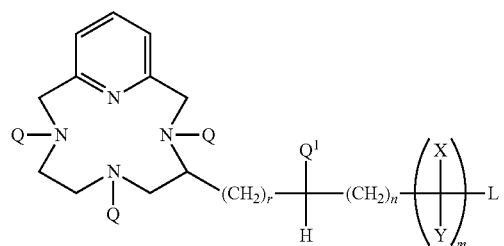

(VIIc)

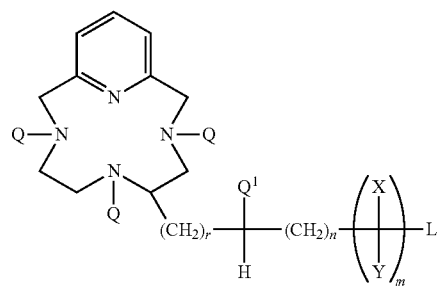

wherein the variables L, X, Y, Q, Q$^1$, m, n and r are as defined above.

The present invention also relates to the bifunctional polyazamacrocyclic chelating agent of formulas (VI) and (VII) above, wherein Q is (CHR$^5$)$_p$CO$_2$R, wherein R, R$^5$ and p are as defined above.

The present invention further provides a bifunctional polyazamacrocyclic chelating agent of formula (VIII):

(VIII)

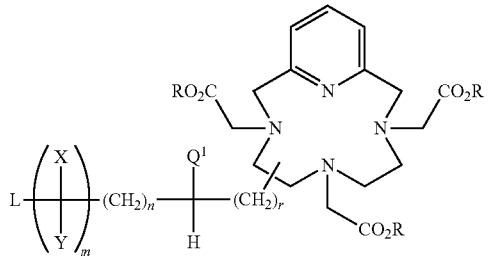

wherein the variables L, X, Y, Q$^1$, R, m, n and r are as defined above.

Examples of the bifunctional polyazamacrocyclic chelating agent of formula (VIII) include chelating agents of the of the formulas (VIIIa) to (VIIIe):

(VIIIa)

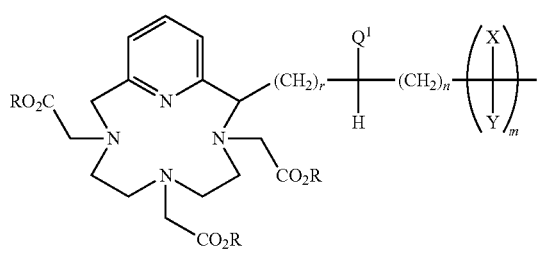

(VIIIb)

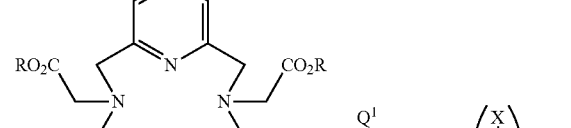

(VIIIc)

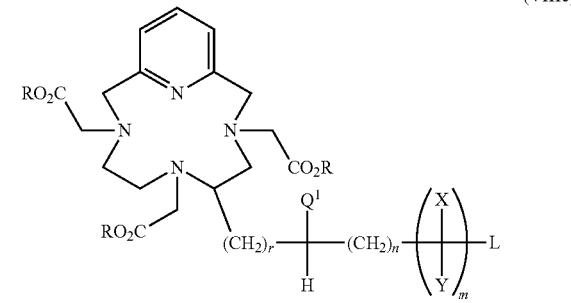

wherein the variables L, X, Y, Q$^1$, R, m, n and r are as defined above.

The present invention also provides a bifunctional polyazamacrocyclic chelating agent of formula (IX):

(IX)

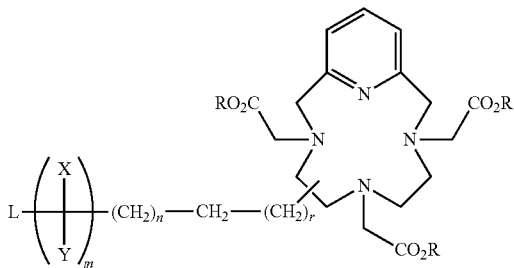

wherein the variables L, X, Y, R, m, n and r are as defined above.

Examples of the bifunctional polyazamacrocyclic chelating agent of formula (IX) include chelating agents of the of the formulas (IXa) to (IXc):

(IXa)

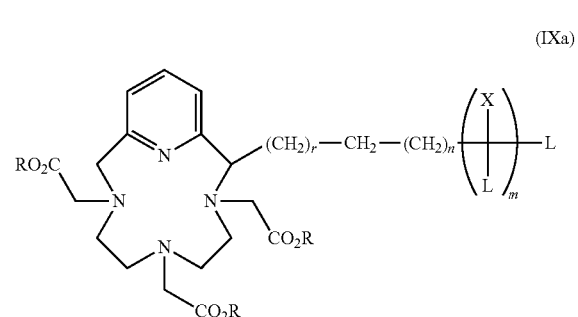

(IXb)

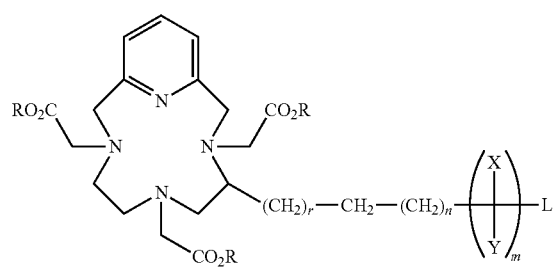

(IXc)

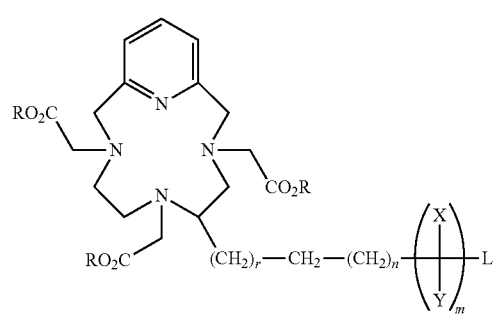

wherein the variables L, X, Y, R, m, n and r are as defined above.

The present invention further provides a bifunctional polyazamacrocyclic chelating agent of formula (X):

(X)

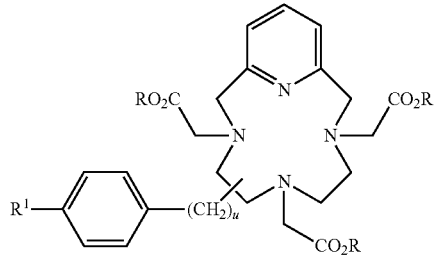

wherein the variables R and $R^1$ are as defined above, and u is 0, 1, 2, 3, 4 or 5.

Examples of the bifunctional polyazamacrocyclic chelating agent of formula (X) include chelating agents of the of the formulas (Xa) to (Xc):

(Xa)

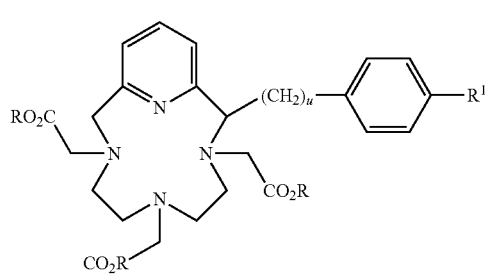

(Xb)

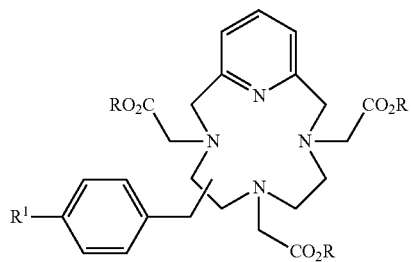

(Xc)

wherein the variables R, $R^1$ and u are as defined above.

The present invention further provides a bifunctional polyazamacrocyclic chelating agent of formula (XI):

(XI)

wherein the variables R and $R^1$ are as defined above.

Examples of the bifunctional polyazamacrocyclic chelating agent of formula (XI) include chelating agents of the of the formulas (XIa) to (XIc):

(XIa)

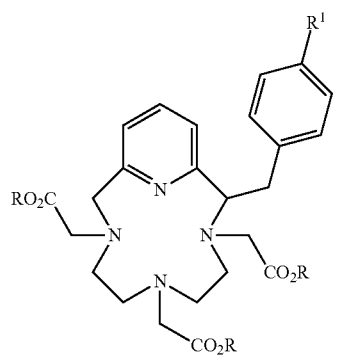

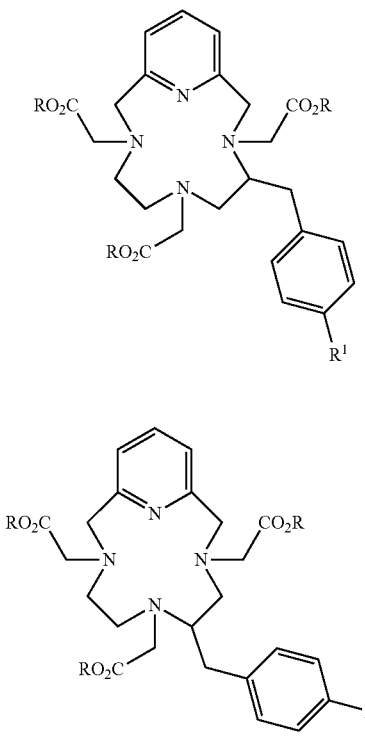

(XIb)

(XIc)

wherein the variables R and R¹ are as defined above.

In another aspect, the present invention relates to a bifunctional polyazamacrocyclic chelating agent of the of the formula (XII):

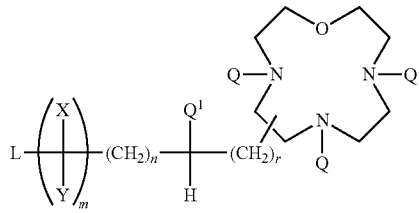

(XII)

wherein the variables L, X, Y, Q, Q¹, m, n and r are as defined above.

Examples of the bifunctional polyazamacrocyclic chelating agent of formula (XII) include chelating agents of the of the formulas (XIIa) to (XIIc):

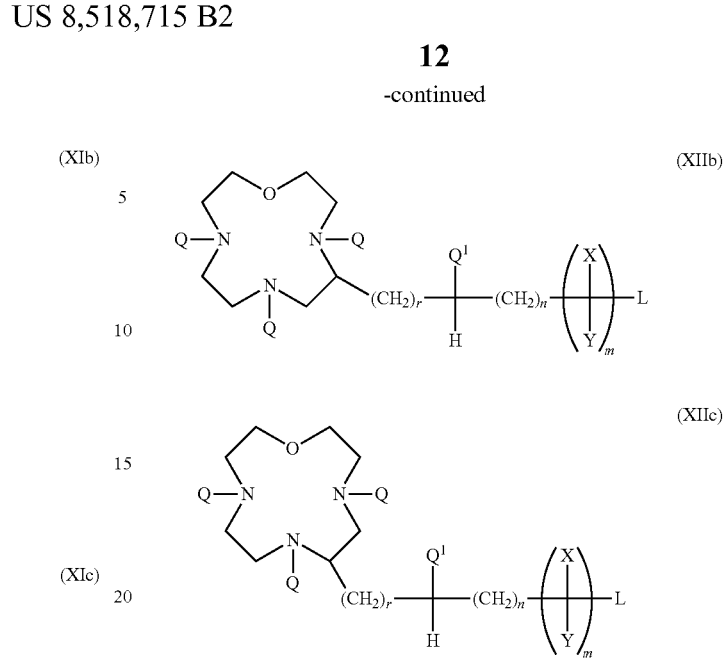

(XIIb)

(XIIc)

wherein the variables L, X, Y, Q, Q¹, m, n and r are as defined above.

The present invention also relates to the bifunctional polyazamacrocyclic chelating agent of formula (XII) above, wherein Q is $(CHR^5)_pCO_2R$, and R, $R^5$ and p are as defined above.

The present invention also provides a bifunctional polyazamacrocyclic chelating agent of formula (XIII):

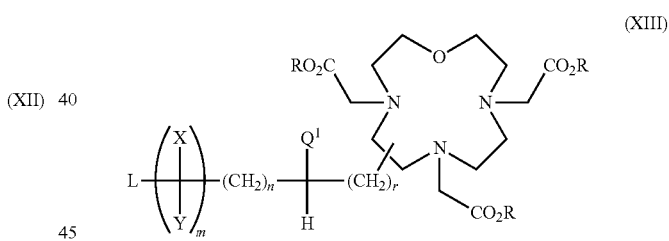

(XIII)

wherein the variables L, X, Y, Q¹, R, m, n and r are as defined above.

Examples of the bifunctional polyazamacrocyclic chelating agent of formula (XIII) include chelating agents of the of the formulas (XIIIa) to (XIIIc):

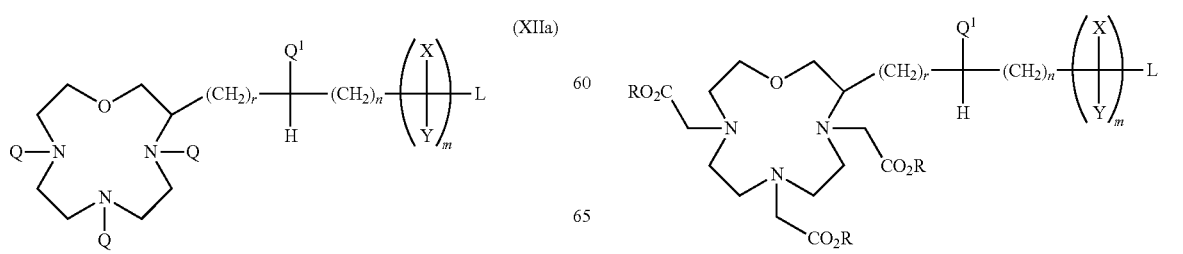

(XIIa)

(XIIIa)

-continued

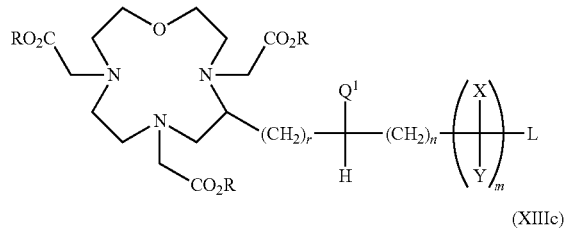
(XIIIb)

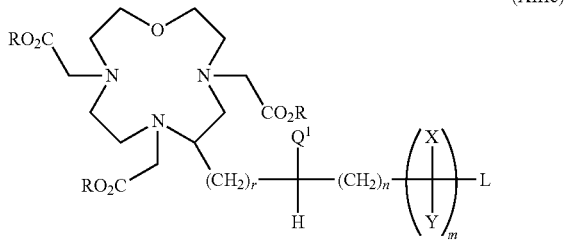
(XIIIc)

wherein the variables L, X, Y, $Q^1$, R, m, n and r are as defined above.

The present invention further provides a bifunctional polyazamacrocyclic chelating agent of formula (XIV):

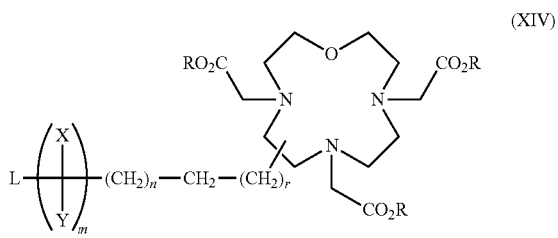
(XIV)

wherein the variables L, X, Y, R, m, n and r are as defined above.

Examples of the bifunctional polyazamacrocyclic chelating agent of formula (XIV) include chelating agents of the of the formulas (XIVa) to (XIVc):

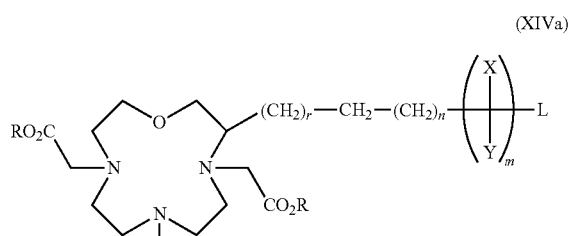
(XIVa)

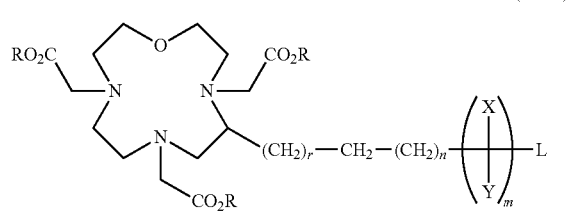
(XIVb)

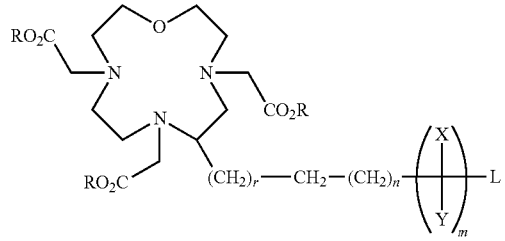
(XIVc)

wherein the variables L, X, Y, R, m, n and r are as defined above.

The present invention also provides a bifunctional polyazamacrocyclic chelating agent of formula (XV):

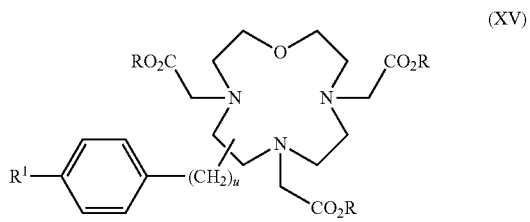
(XV)

wherein the variables R and $R^1$ are as defined above, and u is 0, 1, 2, 3, 4 or 5.

Examples of the bifunctional polyazamacrocyclic chelating agent of formula (XV) include chelating agents of the of the formulas (XVa) to (XVc):

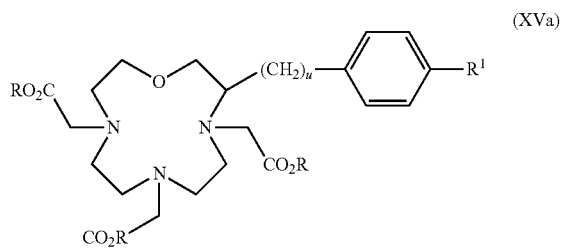
(XVa)

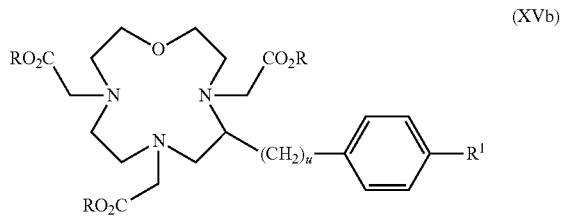
(XVb)

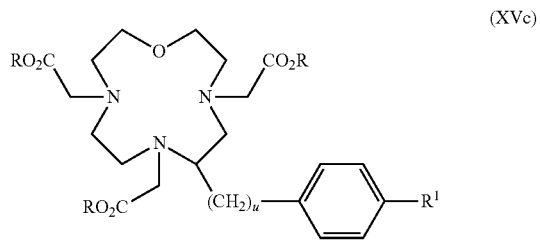
(XVc)

wherein the variables R, $R^1$ and s are as defined above.

The present invention further provides a bifunctional polyazamacrocyclic chelating agent of formula (XVI):

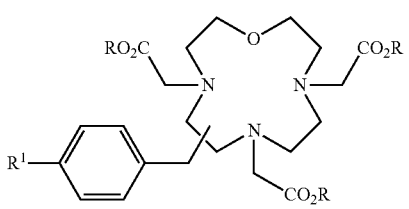

(XVI)

wherein the variables R and R¹ are as defined above.

Examples of the bifunctional polyazamacrocyclic chelating agent of formula (XVI) include chelating agents of the of the formulas (XVIa) to (XVIc):

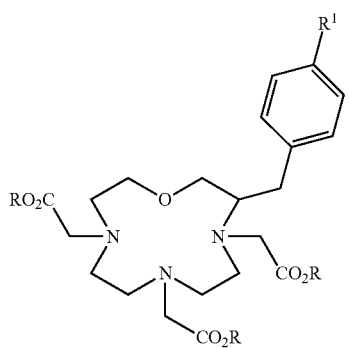

(XVIa)

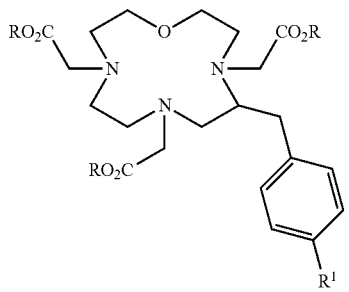

(XVIb)

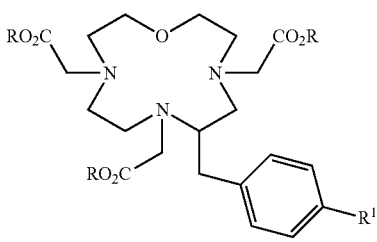

(XVIc)

wherein the variables R and R¹ are as defined above.

The present invention also pertains to the bifunctional polyazamacrocyclic chelating agents of formulas (I), (II), (III), (IV), (IV), (VI), (VIa-f), (VII), (VIIa-c), (VIII), (VIIIa-c), (IX), (IXa-c), (X), (Xa-c), (XI), (XIa-c), (XII), (XIIa-c), (XIII), (XIIIa-c), (XIV), (XIVa-c), (XV), (XVa-c), (XVI), and (XVIa-c), defined above, wherein R¹ is $NO_2$, $NH_2$, isothiocyanato, semicarbazido, thiosemicarbazido, maleimido, bromoacetamido or carboxyl.

In another aspect, the present invention provides a complex comprising the bifunctional polyazamacrocyclic chelating agent of one of formulas (I), (II), (III), (IV), (IV), (VI), (VIa-f), (VII), (VIIa-c), (VIII), (VIIIa-c), (IX), (IXa-c), (X), (Xa-c), (XI), (XIa-c), (XII), (XIIa-c), (XIII), (XIIIa-c), (XIV), (XIVa-c), (XV), (XVa-c), (XVI), and (XVIa-c), defined above, and an ion of a stable or radioactive metal selected from a group consisting of La, Sm, Eu, Gd, Tb, Dy, Ho, Er, Tm, Yb, Lu, Y, Pt, Cu, Re, Tc, Cr, Fe, Mg, Mn and Sc.

In another aspect, the present invention provides a complex comprising the bifunctional polyazamacrocyclic chelating agent of one of formulas (I), (II), (III), (IV), (IV), (VI), (VIa-f), (VII), (VIIa-c), (VIII), (VIIIa-c), (IX), (IXa-c), (X), (Xa-c), (XI), (XIa-c), (XII), (XIIa-c), (XIII), (XIIIa-c), (XIV), (XIVa-c), (XV), (XVa-c), (XVI), and (XVIa-c), defined above, and an ion of a metal selected from a group consisting of $^{90}Y$, $^{177}Lu$, $^{111}In$, $^{64}Cu$, $^{67}Cu$, $^{153}Sm$, $^{153}Gd$, $^{159}Gd$, $^{166}Ho$, $^{149}Pm$, $^{175}Yb$, $^{47}Sc$, $^{142}Pr$, $^{99m}Tc$, $^{188}Re$, $^{186}Re$, $^{67}Ga$, $^{68}Ga$, $^{89}Zr$, and $^{212}Bi$.

In a further aspect, the present invention provides a conjugate comprising one of the complexes defined above covalently attached to a biological carrier, such as a protein, antibody, antibody fragment, hormone, peptide, growth factor, antigen or hapten.

In an even further aspect, the present invention provides a conjugate comprising the bifunctional polyazamacrocyclic chelating agent of one of formulas (I), (II), (III), (IV), (IV), (VI), (VIa-f), (VII), (VIIa-c), (VIII), (VIIIa-c), (IX), (IXa-c), (X), (Xa-c), (XI), (XIa-c), (XII), (XIIa-c), (XIII), (XIIIa-c), (XIV), (XIVa-c), (XV), (XVa-c), (XVI), and (XVIa-c), defined above, covalently attached to a biological carrier, such as a protein, antibody, antibody fragment, hormone, peptide, growth factor, antigen or hapten.

In another aspect, the present invention provides a pharmaceutical composition comprising the conjugate defined above, and a pharmaceutically acceptable carrier.

In another aspect, the present invention provides a method of therapeutic treatment of a mammal having cancer which comprises administering to said mammal a therapeutically effective amount of the pharmaceutical composition defined above.

The chelators of the present application display improved kinetics for complexation to the metal ions $^{90}Y^{3+}$, $^{111}In^{3+}$ and $^{177}Lu^{3+}$ over those for 2,2',2'',2'''-(2-(4-nitrobenzyl)-1,4,7,10-tetraazacyclododecane-1,4,7,10-tetrayl)tetraacetic acid [(±)-p-$NO_2$-Bz-DOTA] and 2,2'-(6-(carboxy(2-methoxy-5-nitrophenyl)methyl)-3,6,9,15-tetraazabicyclo[9.3.1]pentadeca-1(15),11,13-triene-3,9-diyl)diacetic acid [(±)-NPCTA], as well as similar or better stability toward complexation with the metal ions $^{90}Y^{3+}$, $^{111}In^{3+}$ and $^{177}Lu^{3+}$ relative to (±)-p-$NO_2$-Bz-DOTA, and, are, therefore, more suited for therapeutic or diagnostic uses, where rapid complexation and high stability are vitally important to avoid toxic in vivo effects.

Furthermore, the chelators of the present application represent a selection over the chelators generically disclosed in U.S. Pat. Nos. 6,670,456 and 5,403,572, in that they do not include a functionalised cyclic aliphatic or aromatic group capable of forming a bond with a biomolecule connected through one of the nitrogen atoms of their polyazabicyclic core, which can reduce the stability of ions complexed to the chelators.

BRIEF DESCRIPTION OF THE DRAWINGS

These and other features of the invention will become more apparent from the following description in which reference is made to the appended drawings wherein:

BRIEF DESCRIPTION OF THE DRAWINGS

Figure 1:
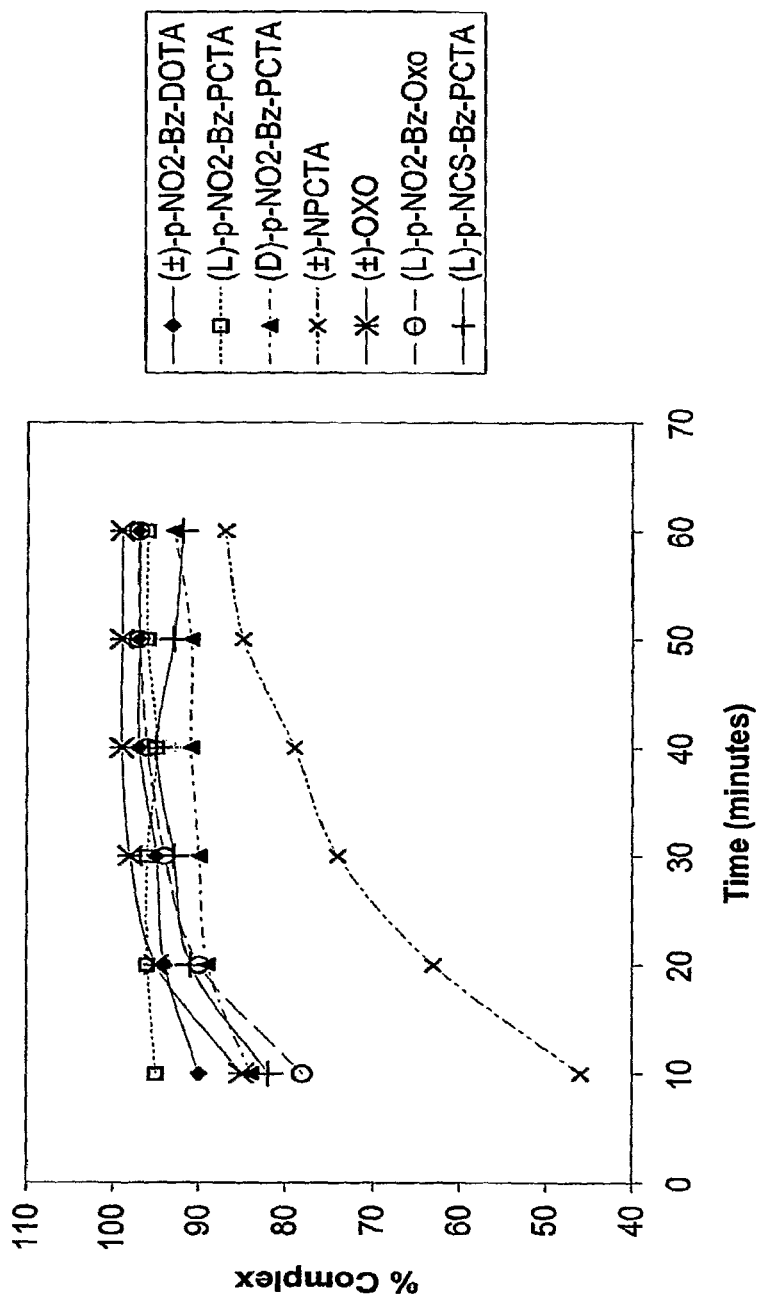

These and other features of the invention will become more apparent from the following description in which reference is made to the appended drawings wherein:

FIG. 1 illustrates the kinetics of complexation of (±)-p-NO$_2$-Bz-DOTA, (L)-p-NO$_2$-Bz-PCTA, (D)-p-NO$_2$-Bz-PCTA, (±)-NPCTA and (±)-OXO with $^{90}$Y$^{3+}$.

Figure 2:
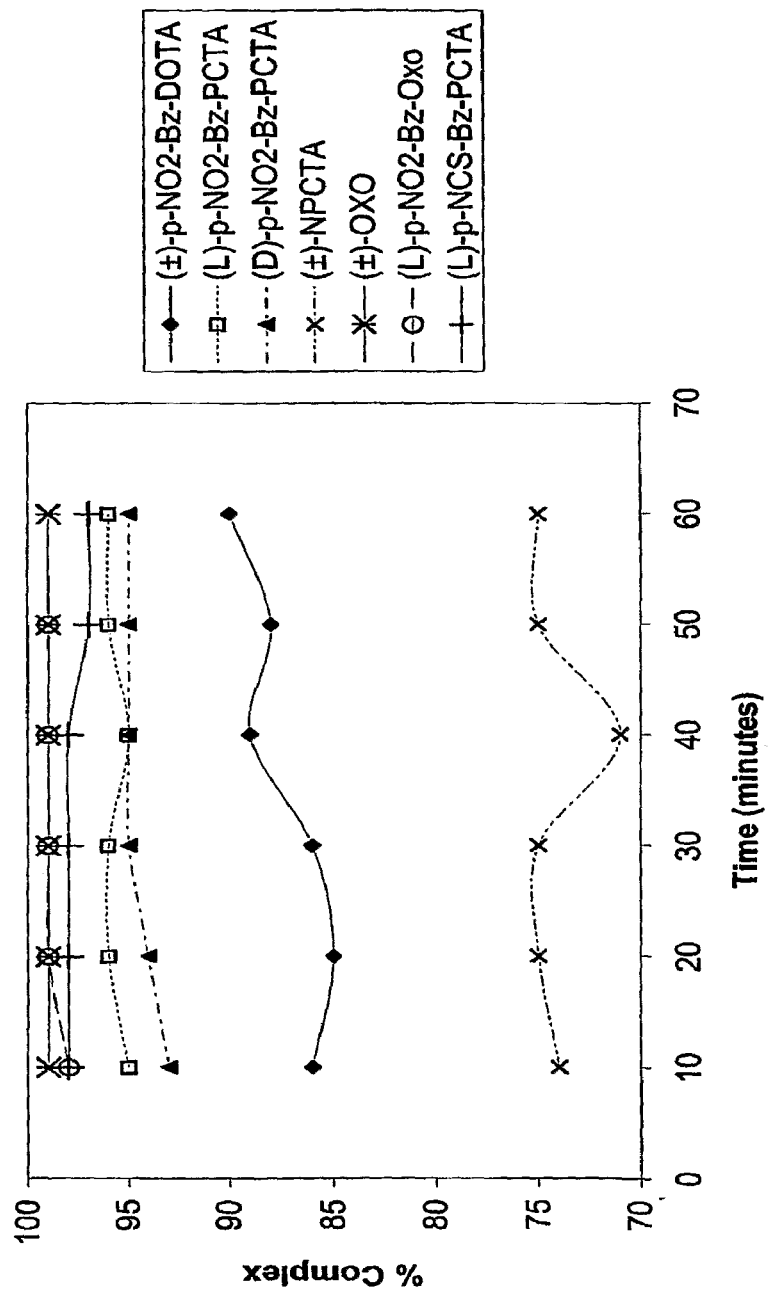

FIG. 2 illustrates the kinetics of complexation of (±)-p-NO$_2$-Bz-DOTA, (L)-p-NO$_2$-Bz-PCTA, (D)-p-NO$_2$-Bz-PCTA, (±)-NPCTA, (±)-OXO and (±)-p-NCS-Bz-PCTA with $^{111}$In$^{3+}$.

Figure 3:
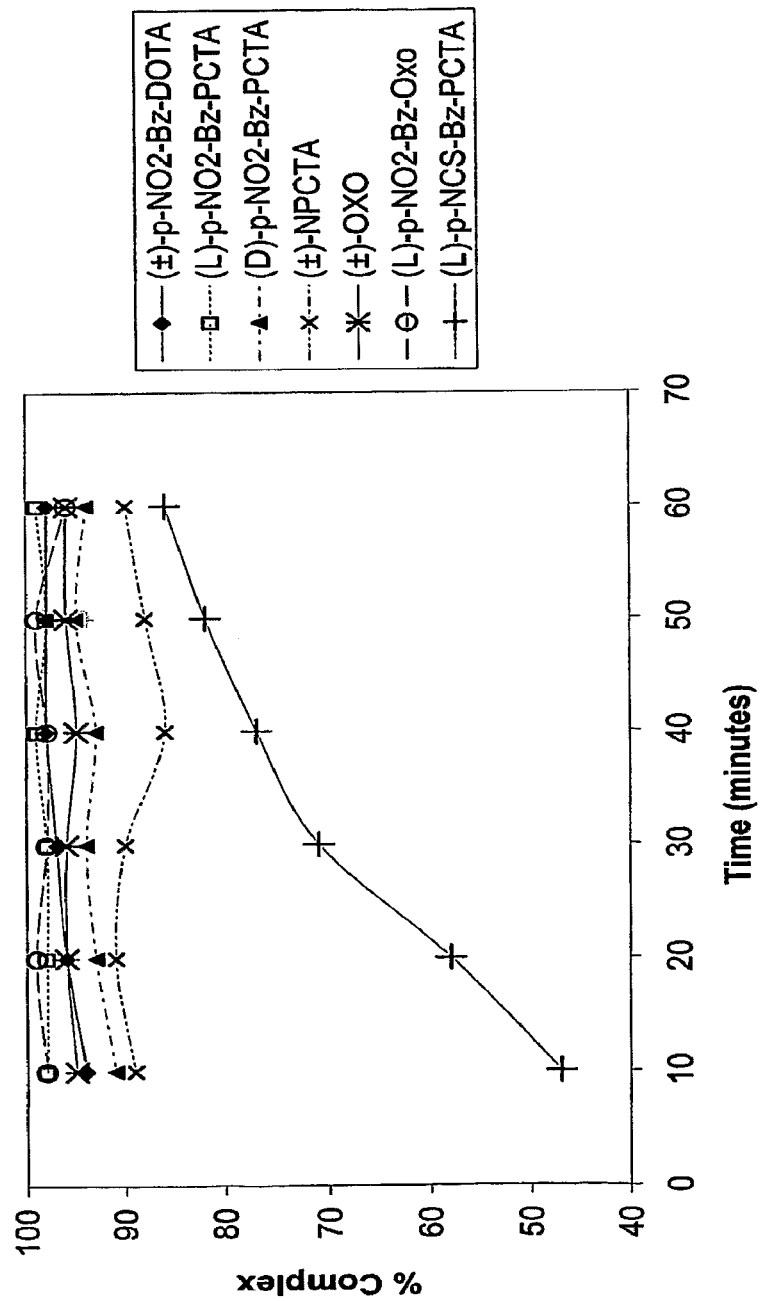

FIG. 3 illustrates the kinetics of complexation of (±)-p-NO$_2$-Bz-DOTA, (L)-p-NO$_2$-Bz-PCTA, (D)-p-NO$_2$-Bz-PCTA, (±)-NPCTA, (±)-OXO and (±)-p-NCS-Bz-PCTA with $^{177}$Lu$^{3+}$.

Figure 4:
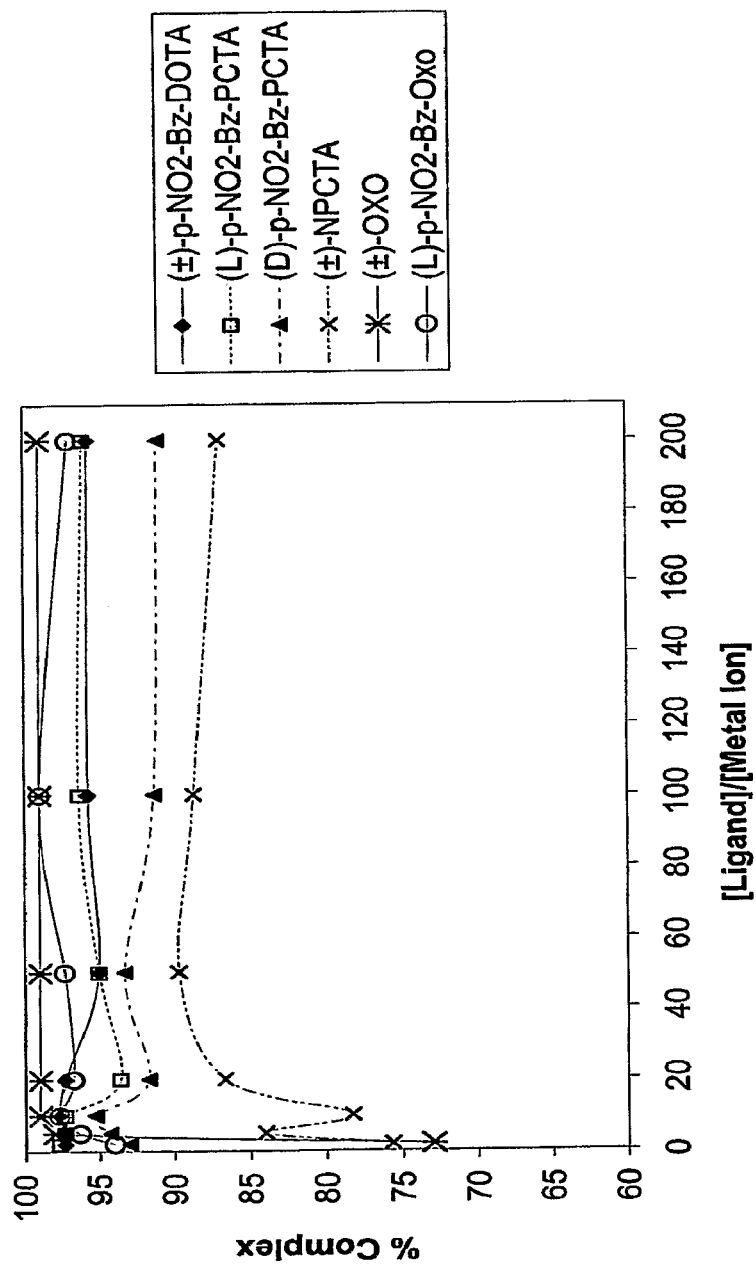

FIG. 4 illustrates the effect of the ligand/metal ion ratio on the percent of complexation of the metal ion to the ligand, where the ligand is (±)-p-NO$_2$-Bz-DOTA, (L)-p-NO$_2$-Bz-PCTA, (D)-p-NO$_2$-Bz-PCTA, (±)-NPCTA or (±)-OXO, and the metal on is $^{90}$Y$^{3+}$.

Figure 5:
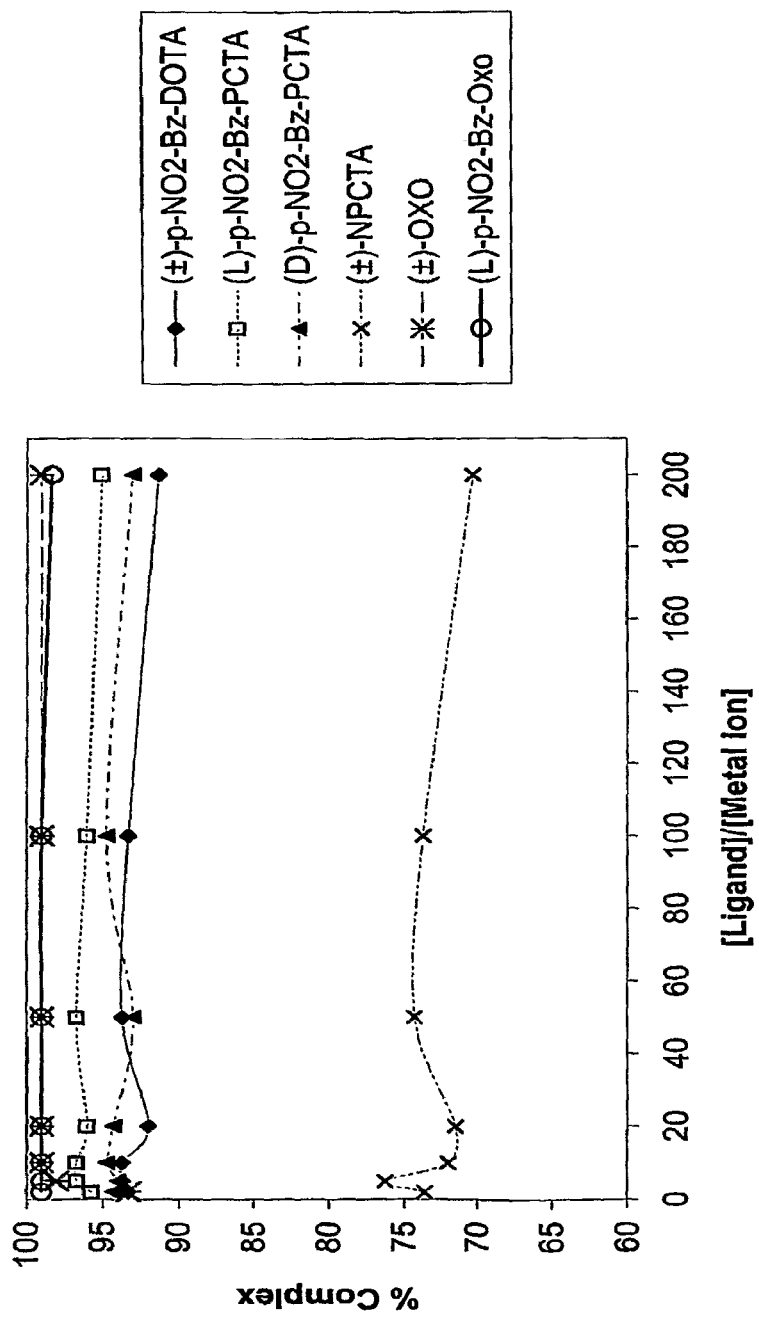

FIG. 5 illustrates the effect of the ligand/metal ion ratio on the percent of complexation of the metal ion to the ligand, where the ligand is (±)-p-NO$_2$-Bz-DOTA, (L)-p-NO$_2$-Bz-PCTA, (D)-p-NO$_2$-Bz-PCTA, (±)-NPCTA or (±)-OXO, and the metal ion is $^{111}$In$^{3+}$.

Figure 6:
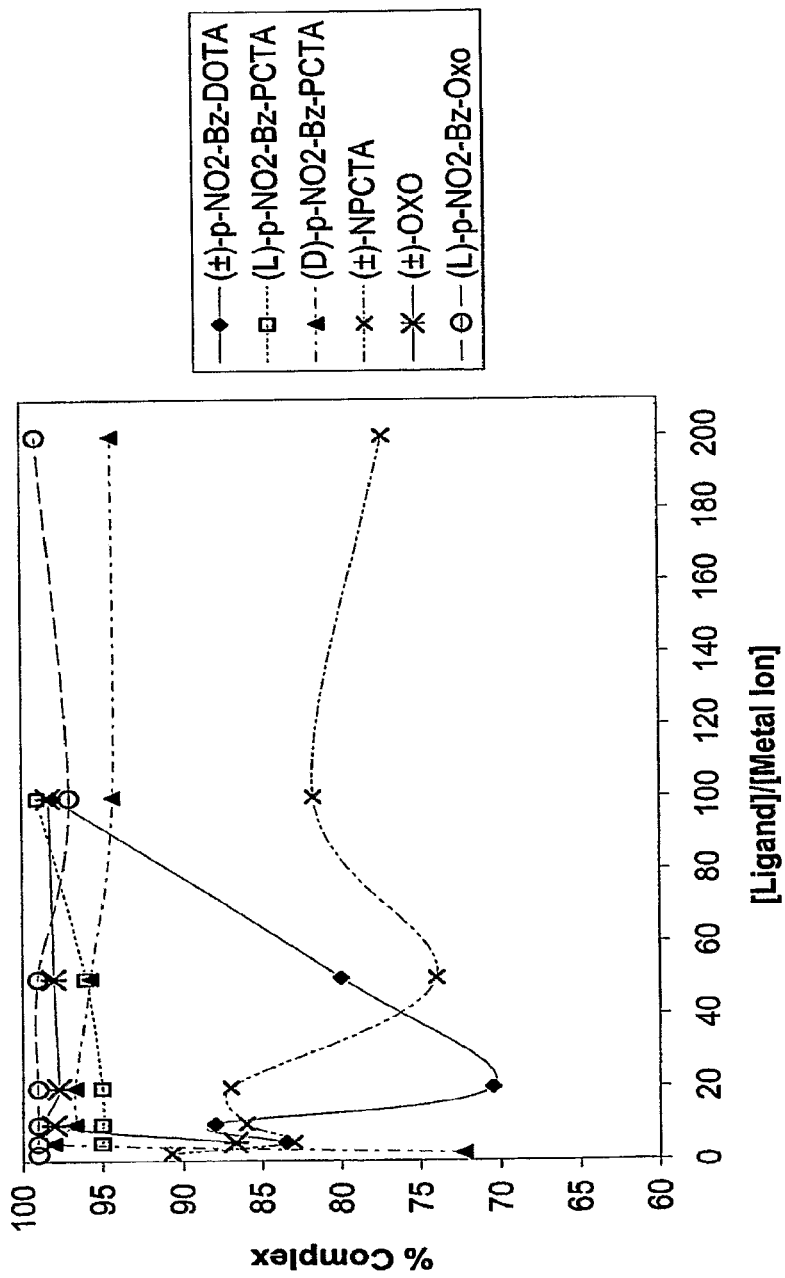

FIG. 6 illustrates the effect of the ligand/metal ion ratio on the percent of complexation of the metal ion to the ligand, where the ligand is (±)-p-NO$_2$-Bz-DOTA, (L)-p-NO$_2$-Bz-PCTA, (D)-p-NO$_2$-Bz-PCTA, (±)-NPCTA or (±)-OXO, and the metal ion is $^{177}$Lu$^{3+}$.

Figure 7:
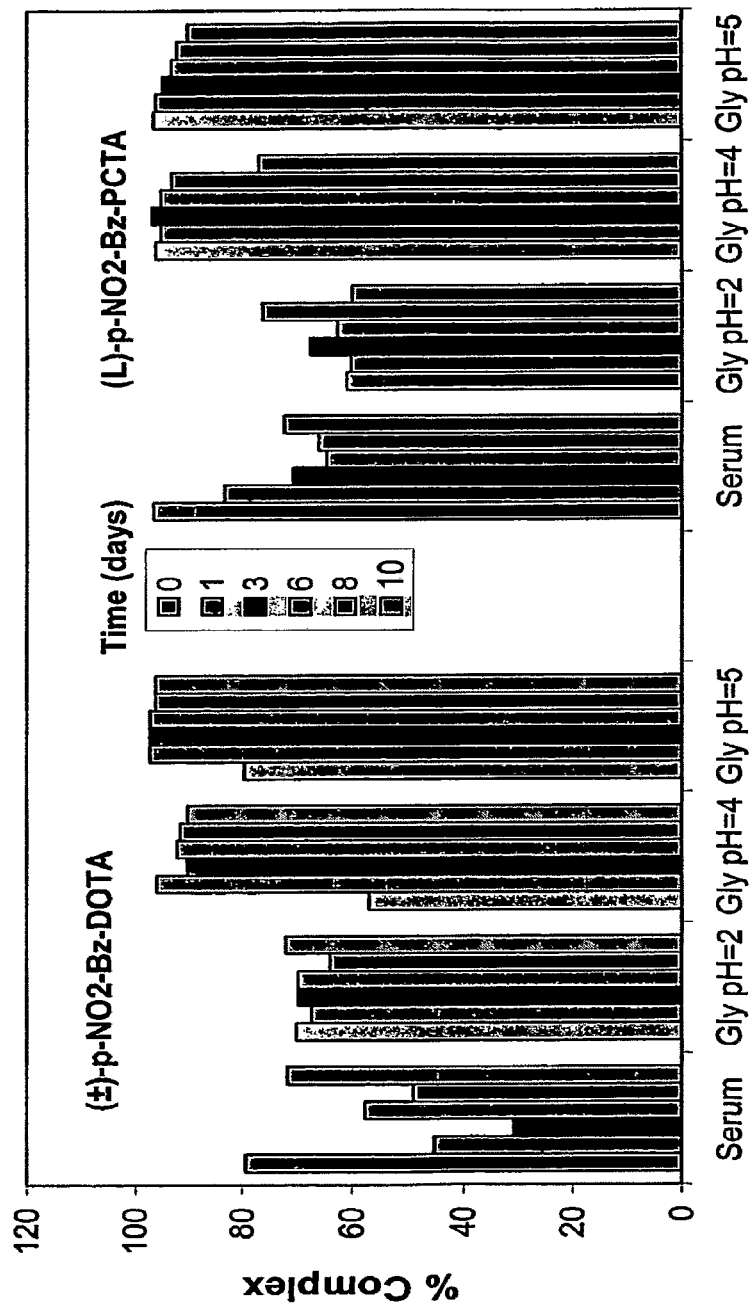

FIG. 7 illustrates the stability of an (±)-p-NO$_2$-Bz-DOTA-$^{90}$Y$^{3+}$ complex and a (L)-p-NO$_2$-Bz-PCTA-$^{90}$Y$^{3+}$ complex in serum, or glycine buffer (pH=2, 4 or 6) as a function of time.

Figure 8:
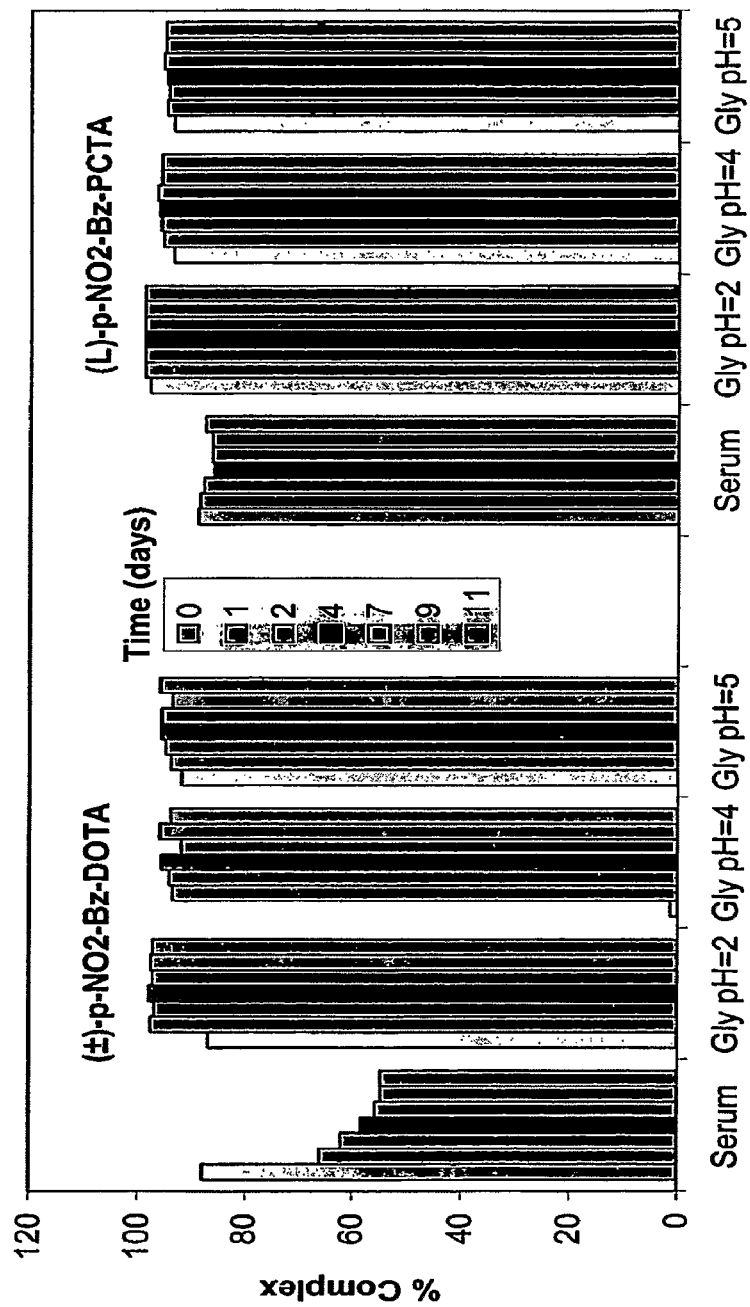

FIG. 8 illustrates the stability of an (±)-p-NO$_2$-Bz-DOTA-$^{111}$In$^{3+}$ complex and a (L)-p-NO$_2$-Bz-PCTA-$^{111}$In$^{3+}$ complex in serum, or glycine buffer (pH=2, 4 or 6) as a function of time.

Figure 9:
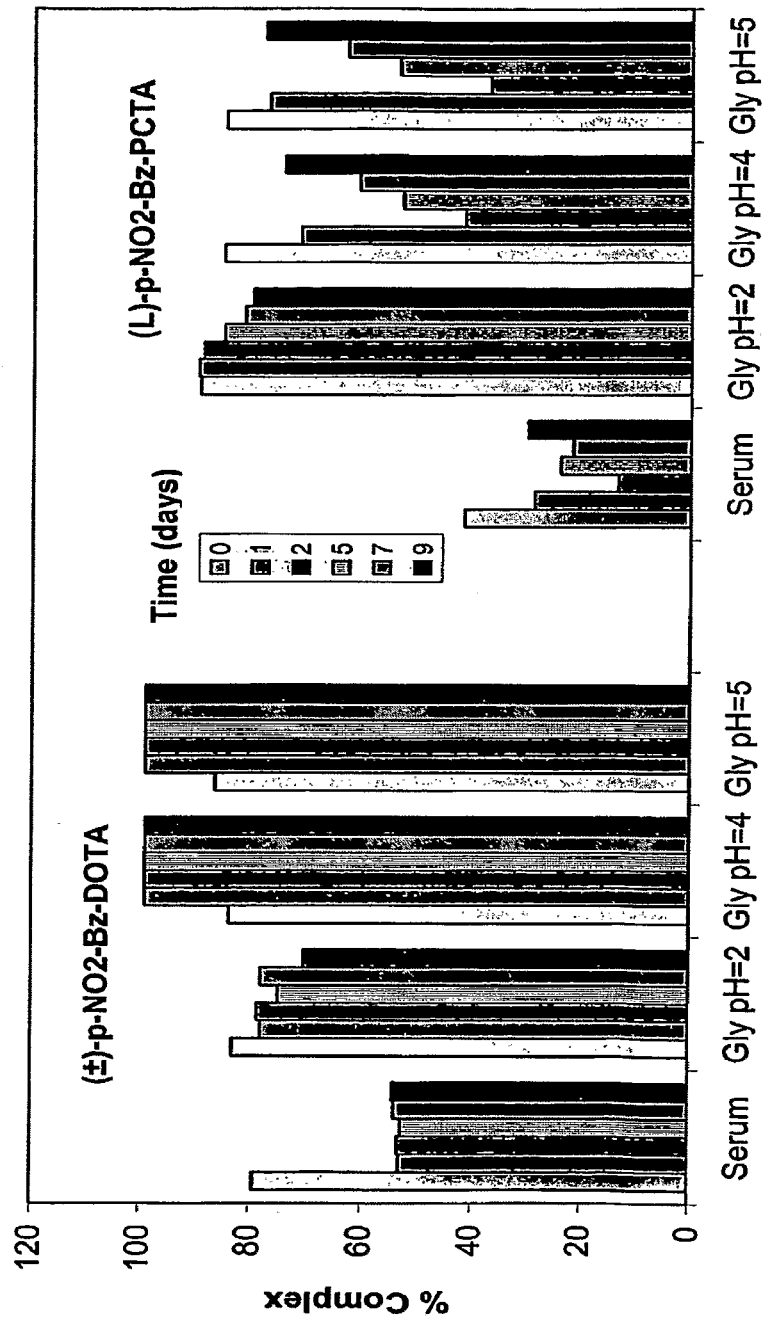

FIG. 9 illustrates the stability of an (±)-p-NO$_2$-Bz-DOTA-$^{177}$Lu$^{3+}$ complex and a (L)-p-NO$_2$-Bz-PCTA-$^{177}$Lu$^{3+}$ complex in serum, or glycine buffer (pH=2, 4 or 6) as a function of time.

DETAILED DESCRIPTION OF THE INVENTION

The present invention relates to bifunctional polyazamacrocyclic chelating agents, to complexes of these chelating agents with metal ions, and to conjugates of these complexes with a biological carrier. More particularly, the present invention relates to ligand structures that exhibit unexpectedly rapid complexation kinetics with the lanthanide series of metal ions. The resulting chelate structures are useful in nuclear medicine applications where efficient and fast metal ion incorporation is a desirable feature.

For the purposes of promoting an understanding of the principles of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

As used herein, "complex" refers to a complex of the compound of the invention, e.g. Formula (I), complexed with a metal ion, where at least one metal atom is chelated or sequestered.

The complexes of the present invention can be prepared by methods well known in the art. Thus, for example, see Chelating Agents and Metal Chelates, Dwyer & Mellor, Academic Press (1964), Chapter 7. See also methods for making amino acids in Synthetic Production and Utilization of Amino Acids, (edited by Kameko, et al.) John Wiley & Sons (1974). An example of the preparation of a complex involves reacting a bicyclopolyazamacrocyclophosphonic acid with a paramagnetic metal ion under aqueous conditions at a pH from 5 to 7. The complex formed is by a chemical bond and results in a stable paramagnetic nuclide composition, e.g. stable to the disassociation of the paramagnetic nuclide from the ligand.

The complexes of the present invention can be formed and administered at a ligand to metal molar ratio of at least about 1:1, from about 1:1 to about 3:1, or more particularly from about 1:1 to about 1.5:1. A large excess of ligand is undesirable since uncomplexed ligand may be toxic to the animal or may result in cardiac arrest or hypocalcemic convulsions.

A "conjugate" refers to a metal ion chelate that is covalently attached to a biological carrier.

As used herein, the term "biological carrier" refers to any biological targeting vector, such as a protein, an antibody, an antibody fragment, a hormone, a peptide, a growth factor, an antigen, a hapten or any other carrier, which functions in this invention to recognize a specific biological target site. Antibody and antibody fragment refers to any polyclonal, monoclonal, chimeric, human, mammalian, single chains, dimeric and tetrameric antibody or antibody fragment. Such biological carrier, when attached to a functionalized complex, serves to carry the attached ion to specific targeted tissues.

The term "bifunctional chelating agent" refers to compounds that have a chelant moiety capable of chelating a metal ion and a moiety covalently bonded to the chelant moiety that is capable of serving as a means to covalently attach to a biological carrier for example, a molecule having specificity for tumor cell epitopes or antigens, such as an antibody or antibody fragment. Such compounds are of great utility for therapeutic and diagnostic applications when they are, for example, complexed with radioactive metal ions and covalently attached to a specific antibody. These types of complexes have been used to carry radioactive metals to tumor cells which are targeted by the specificity of the attached antibody [see, for example, Mears et al., Anal. Biochem. 142, 68-74 (1984); Krejcarek et al., Biochem. And Biophys. Res. Comm. 77, 581-585 (1977)].

The bifunctional chelating agents described herein (represented by Formula I) can be used to chelate or sequester a metal ion to form metal ion chelates (also referred to herein as "complexes", as defined above). The complexes, because of the presence of the functionalizing moiety (represented by R$^1$ in Formula I), can be covalently attached to a biologically active material, such as dextran, molecules that have specific affinity for a receptor, or preferably covalently attached to antibodies or antibody fragments. Thus, the complexes described herein may be covalently attached to an antibody or antibody fragment or have specific affinity for a receptor and are referred to herein as "conjugates".

The term "antibody" refers to a polyclonal antibody, a monoclonal antibody, a chimeric antibody, a heteroantibody, or a fragment thereof. Antibodies used in the present invention may be directed against, for example, cancer, tumors, bacteria, fungi, leukemias, lymphomas, autoimmune disorders involving cells of the immune system, normal cells that need to be ablated such as bone marrow and prostate tissue, virus infected cells including HIV, parasites, mycoplasma, differentiation and other cell membrane antigens, pathogen surface antigens, toxins, enzymes, allergens, drugs and any biologically active molecules. Some examples of antibodies are HuM195 (anti-CD33), CC-11, CC-46, CC-49, CC-49 F(ab')$_2$, CC-83, CC-83 F(ab')$_2$, and B72.3, 1116-NS-19-9

(anti-colorectal carcinoma), 1116-NS-3d (anti-CEA), 703D4 (anti-human lung cancer), 704A1 (anti-human lung cancer) and B72.3. The hybridoma cell lines 1116-NS-19-9, 1116-NS-3d, 703D4, 704A1, CC49, CC83 and B72.3 are deposited with the American Type Culture Collection, having the accession numbers ATCC HB 8059, ATCC CRL 8019, ATCC HB 8301, ATCC HB 8302, ATCC HB 9459, ATCC HB 9453 and ATCC HB 8108, respectively.

Antibody fragment includes Fab fragments and F(ab')$_2$ fragments, and any portion of an antibody having specificity toward a desired epitope or epitopes.

When using the term "radioactive metal chelate/antibody conjugate" or "conjugate", the "antibody" is meant to include whole antibodies and/or antibody fragments, including semi-synthetic or genetically engineered variants thereof. Such antibodies normally have a highly specific reactivity.

The antibodies or antibody fragments which may be used in the conjugates described herein can be prepared by techniques well known in the art. Highly specific monoclonal antibodies can be produced by hybridization techniques well known in the art, see for example, Kohler and Milstein [Nature, 256, 495-497 (1975); and Eur. J. Immunol., 6, 511-519 (1976)]. Such antibodies normally have a highly specific reactivity in the antibody targeted conjugates, antibodies directed against any desired antigen or hapten may be used. Preferably the antibodies which are used in the conjugates are monoclonal antibodies, or fragments thereof having high specificity for a desired epitope(s).

As used herein, "pharmaceutically-acceptable salt" means any salt or mixture of salts of a complex or conjugate of formula (I) which is sufficiently non-toxic to be useful in therapy or diagnosis of animals, preferably mammals. Thus, the salts are useful in accordance with this invention. Representative of those salts formed by standard reactions from both organic and inorganic sources include, for example, sulfuric, hydrochloric, phosphoric, acetic, succinic, citric, lactic, maleic, fumaric, palmitic, cholic, palmoic, mucic, glutamic, gluconic, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium or 1-deoxy-1-(methylamino)-D-glucitol, alkali metal ions, alkaline earth metal ions, and other similar ions. Particularly preferred are the salts of the complexes or conjugates of formula (I) where the salt is potassium, sodium or ammonium. Also included are mixtures of the above salts.

This invention is used with a physiologically acceptable carrier, excipient or vehicle therefor. The methods for preparing such formulations are well known. The formulations may be in the form of a suspension, injectable solution or other suitable formulations. Physiologically acceptable suspending media, with or without adjuvants, may be used.

An "effective amount" of the formulation is used for diagnosis or for therapeutic treatments of diseases. The dose will vary depending on the disease and physical parameters of the animal, such as weight. In vivo diagnostics are also contemplated using formulations of this invention.

Other uses of some of the chelants of the present invention may include the removal of undesirable metals (i.e. iron) from the body, attachment to polymeric supports for various purposes, e.g. as diagnostic agents, and removal of metal ion by selective extraction.

The free acid of the compounds of formula (I) may be used, also the protonated form of the compounds, for example when the carboxylate is protonated and/or the nitrogen atoms, i.e. when the HCl salt is formed.

The complexes so formed can be attached (covalently bonded) to an antibody or fragment thereof and used for therapeutic and/or diagnostic purposes. The complexes and/or conjugates can be formulated for in vivo or in vitro uses. A preferred use of the formulated conjugates is the diagnosis of diseased states (e.g., cancer) in animals, especially humans.

Biotargeted radiopharmaceuticals that employ the chelating agent (ligand) of the present invention to secure a metal radionuclide can be prepared by two methods: 1) Pre-complexation—the metal ligand complex (chelate) can first be prepared followed by covalent attachment of the chelate to a biotargeting group, for example a monoclonal antibody; 2) Post-complexation—a covalent conjugate between the ligand and the biotargeting molecule can be prepared in a first step followed by introduction and complexation of the metal radionuclide. Both methods have merits and shortcomings. Method 1 is appealing from the standpoint that forcing conditions can be utilized to facilitate complexation however subsequent attachment of the complex to a targeting vector requires more elaborate chemical transformation that are difficult to perform rapidly in a hospital setting. In contrast, method 2 is desirable since it allows the more intricate chemistry required for conjugation of the ligand and targeting vector to be performed in controlled environment without time constraints introduced by the radionuclide. The complexation step can then be conducted onsite at the hospital pharmacy by clinical technicians however this step can be problematic since the ligand bound conjugate is much more sensitive to rigorous conditions that favor rapid and complete complexation.

Of the two approaches for preparing biotargeted radiopharmaceuticals, the post-complexation strategy is clearly the most desirable if appropriate ligands and/or conditions can be devised that facilitate rapid and complete incorporation of the radionuclide. The most desirable route to ligand design for the post-complexation approach is based on favorable thermodynamic attributes of macrocyclic polyamines such as cyclen and cyclen analogs. In addition, structural and conformational components can be introduced that can minimize kinetic barriers to complexation. For example, molecular architecture which can enhance pre-organization of the ligand binding site toward the necessary conformational requirements of the metal ion should produce faster complexation kinetics.

The bifunctional chelating agents described herein (represented by formula I) are designed to form stable and inert complexes with the lanthanide series of metals. Complexation kinetics can be modulated by altering backbone structural rigidity, electronic character of the coordinate donor atoms, and conformational accessibility of the metal binding site.

While not wishing to be bound by theory, it is believed that kinetic advantages associated with the present invention are a function of structural modifications that lead to preferred molecular geometries (pre-organization) which match ligating requirements of the metal. In this manner the ligand-metal binding event is accelerated without the need for harsh reaction conditions.

In the context of bifunctional chelating agents, the generation of optimal pre-organized ligand structures conducive to rapid complexation kinetics is significantly influenced by the judicious placement of the linking group. In this manner, the linking group can be engineered to assume a position distant from the metal binding site during the initial stages of the metal docking process followed by the adoption of a secondary conformation induced by complexation that effectively shields the metal form reversible dissociation pathways. The positional orientation of the linking group also affects the electronic nature of the coordinate donor atoms and their juxtaposed lone pair electrons which are critical for satisfying the geometric requirements of the metal ion. The present invention will address this point utilizing comparative examples that exhibit dramatic differences not previously observed or exploited in earlier works.

The present invention also includes formulations comprising the conjugates of this invention and a pharmaceutically acceptable carrier, especially formulations where the pharmaceutically acceptable carrier is a liquid.

The present invention is also directed to a method of therapeutic treatment of a mammal having cancer which comprises administering to said mammal a therapeutically effective amount of the formulation of this invention.

Thus, the present invention may be practiced with the conjugate of the present invention being provided in pharmaceutical formulation, both for veterinary and for human medical use. Such pharmaceutical formulations comprise the active agent (the conjugate) together with a physiologically acceptable carrier, excipient or vehicle therefore. The methods for preparing such formulations are well known. The carrier(s) must be physiologically acceptable in the sense of being compatible with the other ingredient(s) in the formulation and not unsuitably deleterious to the recipient thereof. The conjugate is provided in a therapeutically effective amount, as described above, and in a quantity appropriate to achieve the desired dose.

Complexes of the chelating agent of the present invention with a suitable metal ion, and conjugates of these complexes can be used in diagnostic medical imaging procedures. For example, complexes of the present invention formed with a paramagnetic metal ion, such as $Gd^{+3}$, $Mn^{+2}$ or $Fe^{+3}$, and corresponding conjugates of these complexes can act as contrast agents in magnetic resonance imaging (MRI). In addition, complexes of the present invention formed with a lanthanide metal ion such as, $Tb^{3+}$, $Eu^{3+}$, $Sm^{3+}$ or $Dy^{3+}$, and corresponding conjugates of these complexes can be used in fluorescent imaging procedures.

This invention is used with a physiologically acceptable carrier, excipient or vehicle therefore. The formulations may be in the form of a suspension, injectable solution or other suitable formulations. Physiologically acceptable suspending media, with or without adjuvants, may be used.

The formulations include those suitable for parenteral (including subcutaneous, intramuscular, intraperitoneal, and intravenous), oral, rectal, topical, nasal, or ophthalmic administration. Formulations may be prepared by any methods well known in the art of pharmacy. Such methods include the step of bringing the conjugate into association with a carrier, excipient or vehicle therefore. In general, the formulation may be prepared by uniformly and intimately bringing the conjugate into association with a liquid carrier, a finely divided solid carrier, or both, and then, if necessary, shaping the product into desired formulation. In addition, the formulations of this invention may further include one or more accessory ingredient(s) selected from diluents, buffers, binders, disintegrants, surface active agents, thickeners, lubricants, preservatives, and the like. In addition, a treatment regime might include pretreatment with non-radioactive carrier.

Injectable compositions of the present invention may be either in suspension or solution form. In the preparation of suitable formulations it will be recognized that, in general, the water solubility of the salt is greater than the acid form. In solution form the complex (or when desired the separate components) is dissolved in a physiologically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions contain no more than 50 percent of the organic solvent by volume.

Injectable suspensions are compositions of the present invention that require a liquid suspending medium, with or without adjuvants, as a carrier. The suspending medium can be, for example, aqueous polyvinylpyrrolidone, inert oils such as vegetable oils or highly refined mineral oils, polyols, or aqueous carboxymethylcellulose. Suitable physiologically acceptable adjuvants, if necessary to keep the complex in suspension, may be chosen from among thickeners such as carboxymethylcellulose, polyvinylpyrrolidone, gelatin, and the alginates. Many surfactants are also useful as suspending agents, for example, lecithin, alkylphenol, polyethyleneoxide adducts, naphthalenesulfonates, alkylbenzenesulfonates, and polyoxyethylene sorbitan esters.

General synthetic approach to a twelve-membered macrocyclic, bifunctional chelant of the present invention as represented by formula I involves the use of functionalized moieties in the formation of the twelve-membered tetraazamacrocycle in order to accomplish backbone substitution. Various synthetic routes to functionalized chelants of formula I can be envisioned by substituting these moieties into the schemes presented in U.S. Pat. Nos. 5,428,139; 5,480,990; and 5,739,294.

More specifically, compounds of formula (XI) can be synthesized based on a modification of the original synthetic procedure for PCTA (2,2',2"-(3,6,9,15-tetraazabicyclo[9.3.1] pentadeca-1(15),11,13-triene-3,6,9-triyl)triacetic acid) provided in Stetter et al. (Stetter, H.; Frank, W.; Mertens, R. Preparation and complexation of polyazacycloalkane-N-acetic acids. *Tetrahedron* (1981), 37(4), 767-72, or in Aime et al. (Aime, S.; Botta, M.; Crich, S. G.; Giovenzana, G. B.; Jommi, G.; Pagliarin, R.; Sisti, M. *Inorg. Chem.* 1997, 36, 2992-3000), the disclosures of which is incorporated herein by reference.

Scheme 1 illustrates an example of a method that can be used to produce a compound of formula (XIb). This method involves cyclizing 2,6-bis(chloromethyl)pyridine (XXIII) with (XXII) in DMF to produce (XXIV), followed by deprotection and alkylation of 4-(4-nitrobenzyl)-3,6,9-tritosyl-3,6, 9,15-tetraazabicyclo[9.3.1]pentadeca-1(15),11,13-triene (XXIV) using bromoacetic acid to yield 2,2',2"-(4-(4-nitrobenzyl)-3,6,9,15-tetraazabicyclo[9.3.1]pentadeca-1(15), 11,13-triene-3,6,9-triyl)triacetic acid (XXV). Hydrogenation of the nitro group of (XXV) is then achieved using 10% palladium on carbon catalyst at ambient pressure to give aniline intermediate 2,2',2"-(4-(4-aminobenzyl)-3,6,9,15-tetraazabicyclo[9.3.1]pentadeca-1(15),11,13-triene-3,6,9-triyl)triacetic acid (XXVI). Conversion of the aniline (XXVI) to the reactive electrophilic isothiocyanate 2,2',2"-(4-(4-isothiocyanatobenzyl)-3,6,9,15-tetraazabicyclo[9.3.1]pentadeca-1(15),11,13-triene-3,6,9-triyl)triacetic acid (XXVII) is carried out using a 2-phase reaction medium with chloroform/water and thiophosgene.

Scheme 1. Synthetic method of producing compound (XXV) and nucleophilic and electrophilic derivatives thereof.

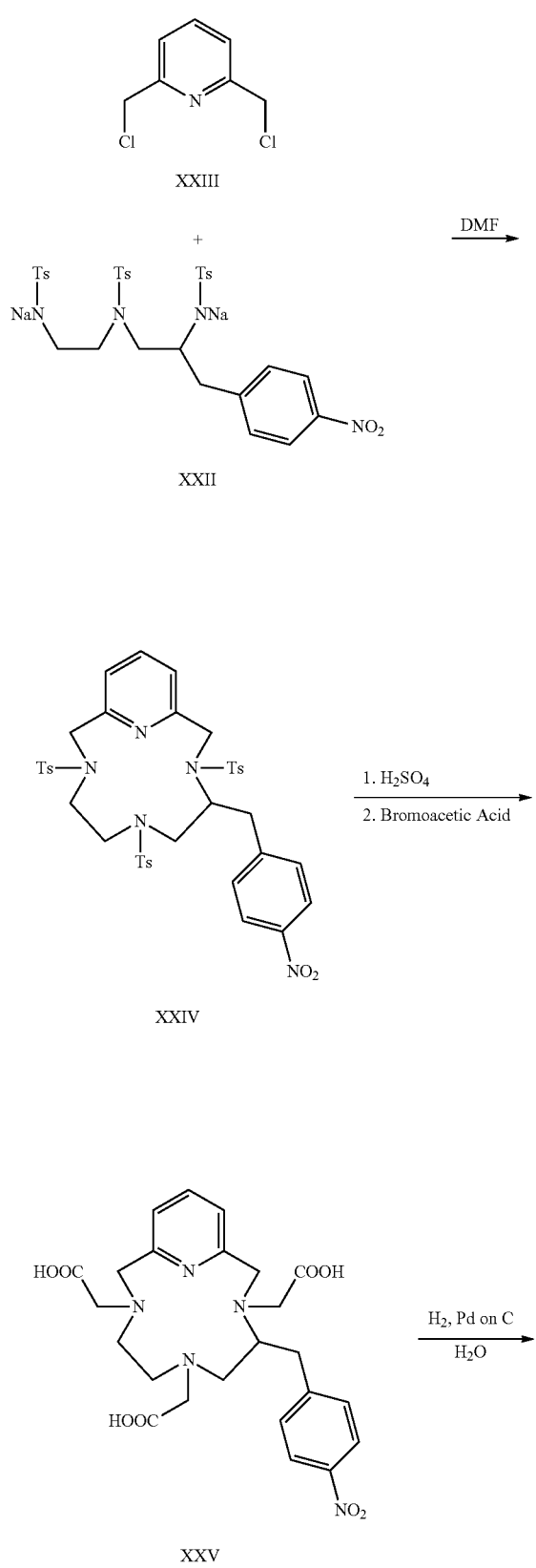

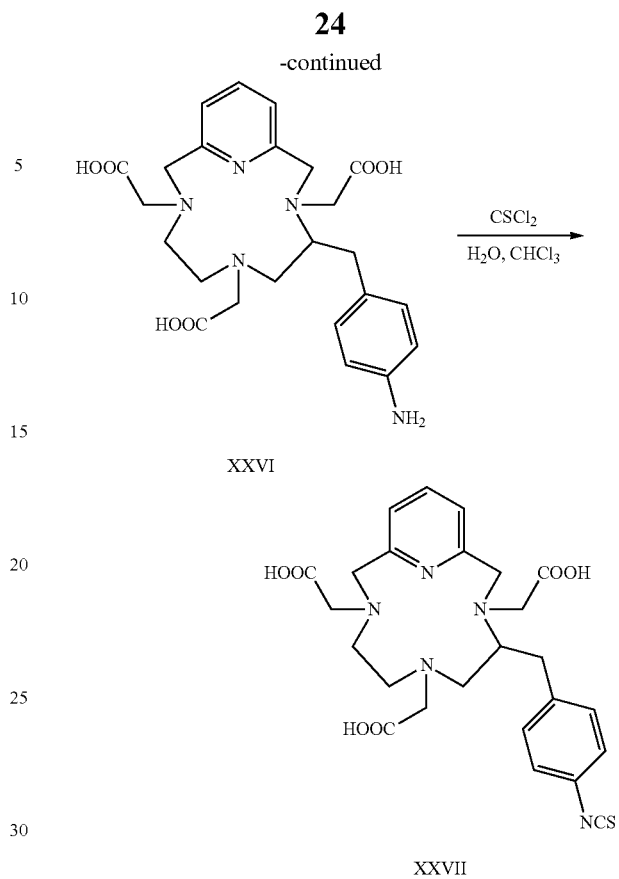

Intermediate XXII is prepared based on the synthetic approach shown in Scheme 2. $N^1$-(2-aminoethyl)-3-(4-nitrophenyl)propane-1,2-diamine (XX) is protected using tosyl chloride and triethylamine to afford tritosylated compound 4-methyl-N-(2-(4-methylphenylsulfonamido)-3-(4-nitrophenyl)propyl)-N-(2-(4-methylphenylsulfonamido)ethyl) benzenesulfonamide (XXI). Deprotonation of (XXI) with sodium ethoxide in ethanol produces a disodium salt of compound (XXI), compound (XXII). Compound (XX) is produced according to the method of Corson et al. (Corson, D. T.; Meares, C. F. *Bioconjugate Chem.* 2000, 11, 292-299, the disclosure of which is incorporated herein by reference).

Scheme 2. Synthetic method of producing intermediate (XXII).

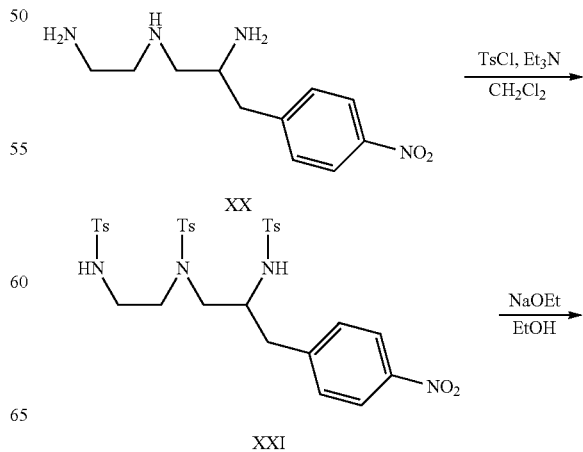

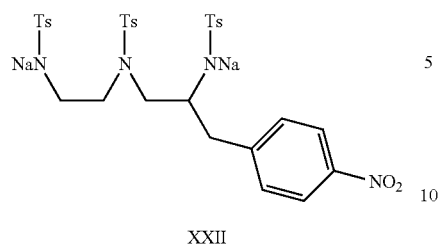

XXII

In another example, compounds of formula (XVIb) can be synthesized based on a modification of the original synthetic procedure for OXO-DO3A (2,2',2''-(1-oxa-4,7,10-triazacyclododecane-4,7,10-triyl)triacetic acid) set forth in Amorim et al. (Amorim, M. T. S.; Delgado, Rita; Frausto da Silva, J. J. R.; Candida, M.; Vaz, T. A.; Vilhena, M. Fernando. Metal complexes of 1-oxa-4,7,10-triazacyclododecane-N,N',N''-triacetic acid. Cent. Quim. Estrut., Inst. Super. Tec., Lisbon, Port. Talanta (1988), 35(9), 741-5, the disclosure of which is incorporated by reference herein).

Scheme 3 illustrates an example of a method that can be used to produce a compound of formula (XVIb). This method involves cyclizing 2,2'-oxybis(ethane-2,1-diyl)bis(4-methylbenzenesulfonate) (XXVIII) with (XXII) in DMF to produce 5-(4-nitrobenzyl)-1-oxa-4,7,10-triazacyclododecane-4,7,10-triyl tris(4-methylbenzenesulfonate) (XXIX), followed by deprotection and alkylation of (XXIX) using bromoacetic acid to yield 2,2',2''-(5-(4-nitrobenzyl)-1-oxa-4,7,10-triazacyclododecane-4,7,10-triyl)triacetic acid (XXX). Hydrogenation of the nitro group of (XXX) is then achieved using 10% palladium on carbon catalyst at ambient pressure to give aniline intermediate 2,2',2''-(5-(4-aminobenzyl)-1-oxa-4,7,10-triazacyclododecane-4,7,10-triyl)triacetic acid (XXXI). Conversion of (XXXI) to the reactive electrophilic isothiocyanate 2,2',2''-(5-(4-isothiocyanatobenzyl)-1-oxa-4,7,10-triazacyclododecane-4,7,10-triyl)triacetic acid (XXXII) is carried out using a 2-phase reaction medium with chloroform/water and thiophosgene.

Scheme 3. Synthetic method of producing compound (XXX) and nucleophilic and electrophilic derivatives thereof.

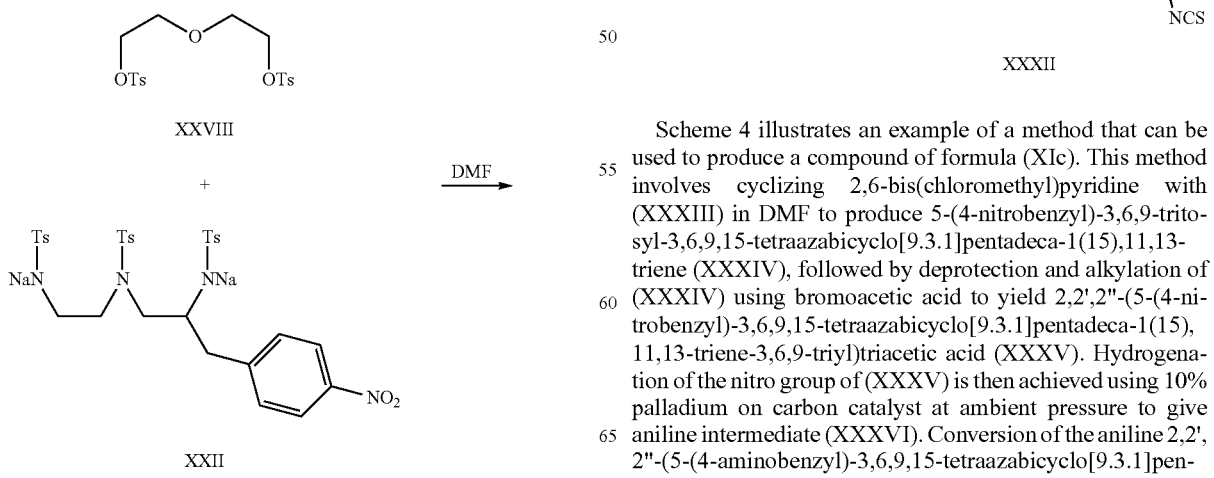

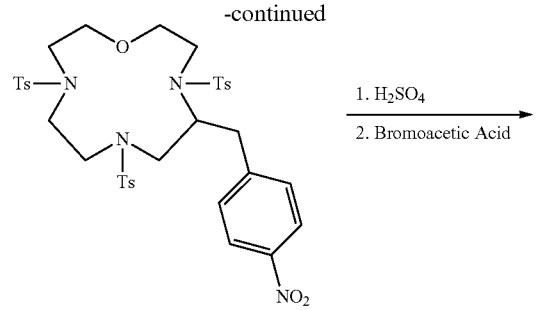

Scheme 4 illustrates an example of a method that can be used to produce a compound of formula (XIc). This method involves cyclizing 2,6-bis(chloromethyl)pyridine with (XXXIII) in DMF to produce 5-(4-nitrobenzyl)-3,6,9-tritosyl-3,6,9,15-tetraazabicyclo[9.3.1]pentadeca-1(15),11,13-triene (XXXIV), followed by deprotection and alkylation of (XXXIV) using bromoacetic acid to yield 2,2',2''-(5-(4-nitrobenzyl)-3,6,9,15-tetraazabicyclo[9.3.1]pentadeca-1(15),11,13-triene-3,6,9-triyl)triacetic acid (XXXV). Hydrogenation of the nitro group of (XXXV) is then achieved using 10% palladium on carbon catalyst at ambient pressure to give aniline intermediate (XXXVI). Conversion of the aniline 2,2',2''-(5-(4-aminobenzyl)-3,6,9,15-tetraazabicyclo[9.3.1]pentadeca-1(15),11,13-triene-3,6,9-triyl)triacetic acid (XXXVI)

to the reactive electrophilic isothiocyanate 2,2′,2″-(5-(4-isothiocyanatobenzyl)-3,6,9,15-tetraazabicyclo[9.3.1]pentadeca-1(15),11,13-triene-3,6,9-triyl)triacetic acid (XXXVII) is carried out using a 2-phase reaction medium with chloroform/water and thiophosgene.

Scheme 4. Synthetic method of producing compounds (XXXV) and nucleophilic and electrophilic derivatives thereof.

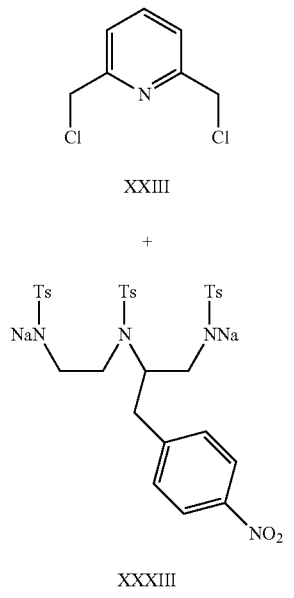
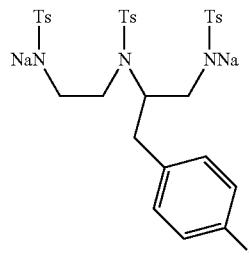
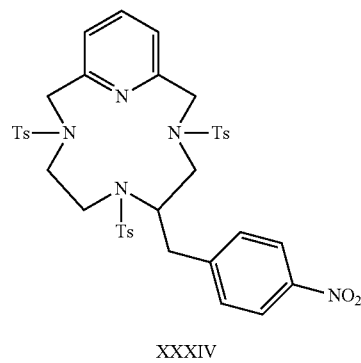
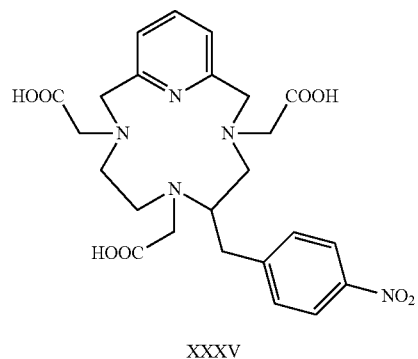
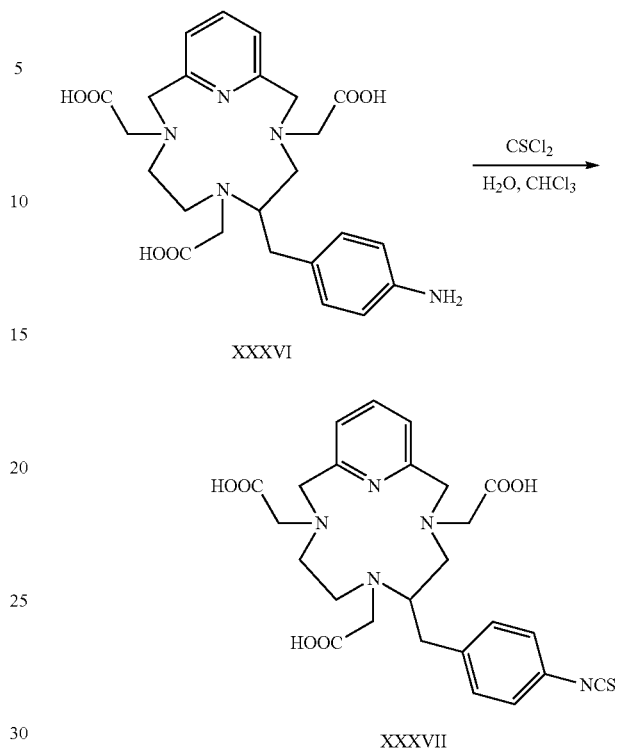

Intermediate XXXIII is prepared based on the synthetic approach shown in Scheme 5. The compound methyl 2-amino-3-(4-nitrophenyl)propanoate (XXXVIII), produced by treating methyl 2-amino-3-(4-nitrophenyl)propanoate hydrochloride with triethylamine, is allowed to react with methyl 2-bromoacetate and diisopropylethylamine to produce methyl 2-(2-methoxy-2-oxoethylamino)-3-(4-nitrophenyl)propanoate (XXXIX). The compound 2-(2-amino-2-oxoethylamino)-3-(4-nitrophenyl)propanamide (IL) is produced by treating (XXXIX) with ammonia in methanol. Reduction of (IL) with BH$_3$ in THF affords N2-(2-aminoethyl)-3-(4-nitrophenyl)propane-1,2-diamine (ILI). Protection of the amino groups of (ILI) with tosyl chloride yields 4-methyl-N-(1-(4-methylphenylsulfonamido)-3-(4-nitrophenyl)propan-2-yl)-N-(2-(4-methylphenylsulfonamido)ethyl)benzenesulfonamide (ILII). Deprotonation of the terminal amino groups of (ILII) results in the formation of the disodium salt (XXXIII).

Scheme 5. Synthetic method of producing intermediate (XXXIII).

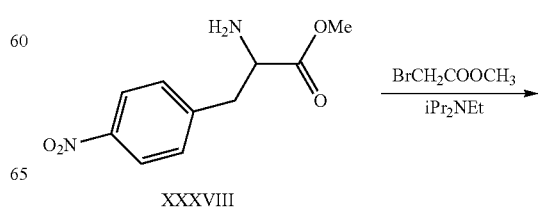

involves cyclizing 2,2'-oxybis(ethane-2,1-diyl)bis(4-methylbenzenesulfonate) (XXIII) with (XXXIII) in DMF to produce 6-(4-nitrobenzyl)-4,7,10-tritosyl-1-oxa-4,7,10-triazacyclododecane (ILIII), followed by deprotection and alkylation of (ILIII) using bromoacetic acid to yield 2,2',2"-(6-(4-nitrobenzyl)-1-oxa-4,7,10-triazacyclododecane-4,7,10-triyl)triacetic acid (ILIV). Hydrogenation of the nitro group of (ILIV) is then achieved using 10% palladium on carbon catalyst at ambient pressure to give aniline intermediate 2,2',2"-(6-(4-aminobenzyl)-1-oxa-4,7,10-triazacyclododecane-4,7,10-triyl)triacetic acid (ILV). Conversion of the aniline (ILV) to the reactive electrophilic isothiocyanate 2,2',2"-(6-(4-isothiocyanatobenzyl)-1-oxa-4,7,10-triazacyclododecane-4,7,10-triyl)triacetic acid (ILVI) is carried out using a 2-phase reaction medium with chloroform/water and thiophosgene.

Scheme 6. Synthetic method of producing compound (ILIV) and nucleophilic and electrophilic derivatives thereof.

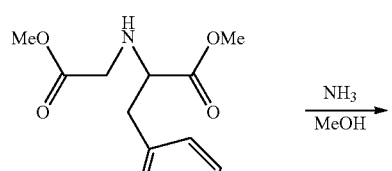

XXXIX

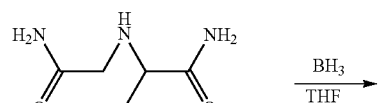

IL

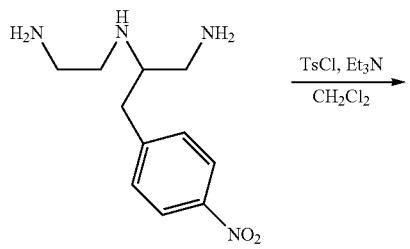

ILI

ILII

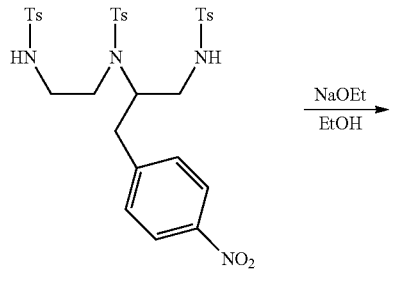

XXXIII

Scheme 6 illustrates an example of a method that can be used to produce a compound of formula (XVIc). This method

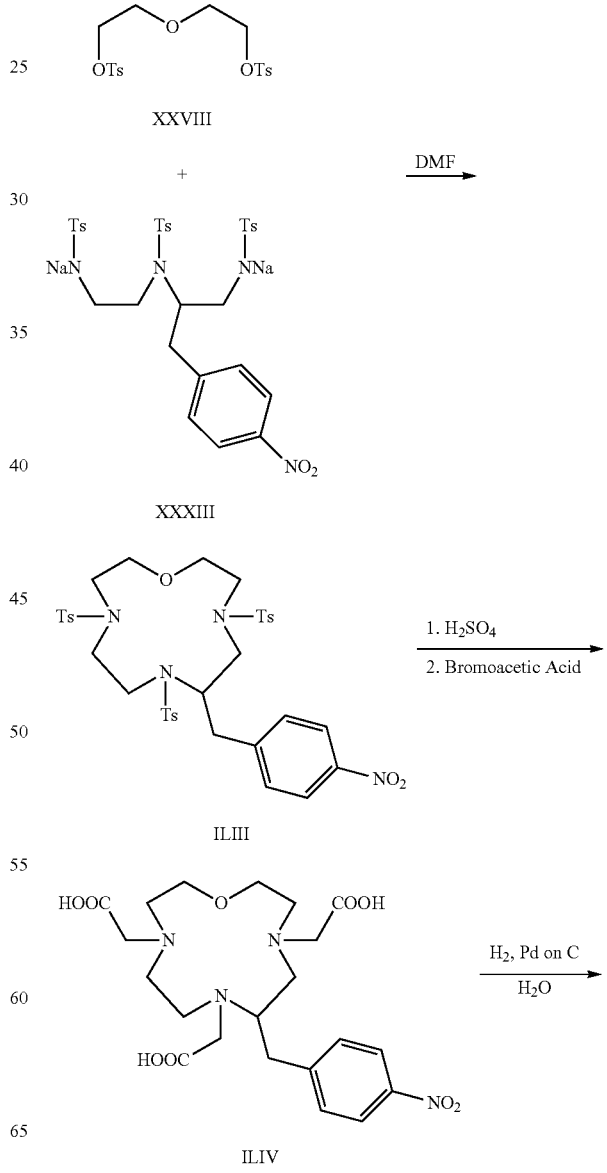

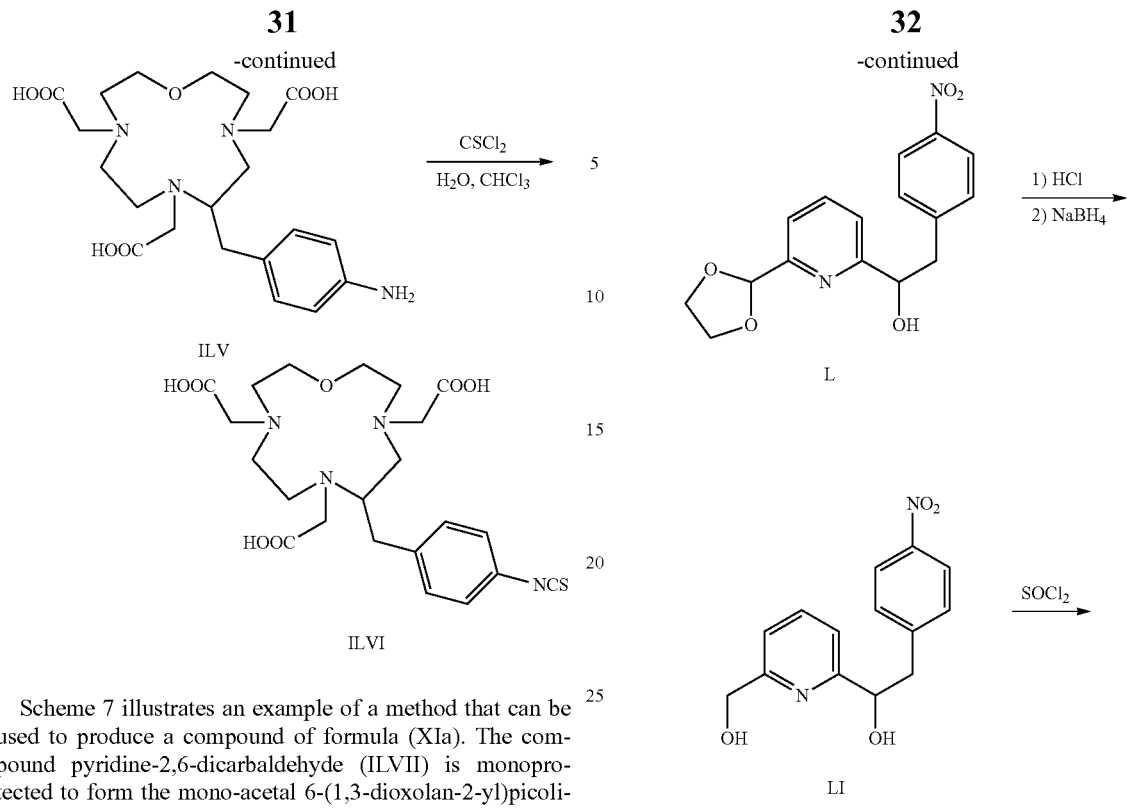

Scheme 7 illustrates an example of a method that can be used to produce a compound of formula (XIa). The compound pyridine-2,6-dicarbaldehyde (ILVII) is monoprotected to form the mono-acetal 6-(1,3-dioxolan-2-yl)picolinaldehyde (ILVIII). Reaction of (ILVIII) with the Grignard reagent (4-nitrobenzyl)magnesium bromide (ILIX) produces the alcohol 1-(6-(1,3-dioxolan-2-yl)pyridin-2-yl)-2-(4-nitrophenyl)ethanol (L). The alcohol (L) is deprotected with HCl, and the resulting aldehyde is reduced with NaBH$_4$ to produce the diol 1-(6-(hydroxymethyl)pyridin-2-yl)-2-(4-nitrophenyl)ethanol (LI). Chlorination of (LI) with thionyl chloride yields the compound 2-(1-chloro-2-(4-nitrophenyl)ethyl)-6-(chloromethyl)pyridine (LH). Cyclization of (LII) with (LIII) results in the product 2-(4-nitrobenzyl)-3,6,9-tritosyl-3,6,9,15-tetraazabicyclo[9.3.1]pentadeca-1(15),11,13-triene (LIV). Finally, deprotection of (LIV) and alkylation with bromoacetic acid produces the compound 2,2',2''-(2-(4-nitrobenzyl)-3,6,9,15-tetraazabicyclo[9.3.1]pentadeca-1(15),11,13-triene-3,6,9-triyl)triacetic acid (LV). The nitro group of the compound (LV) can be converted to corresponding amino and isothiocyante derivatives according to the same methods outlined above.

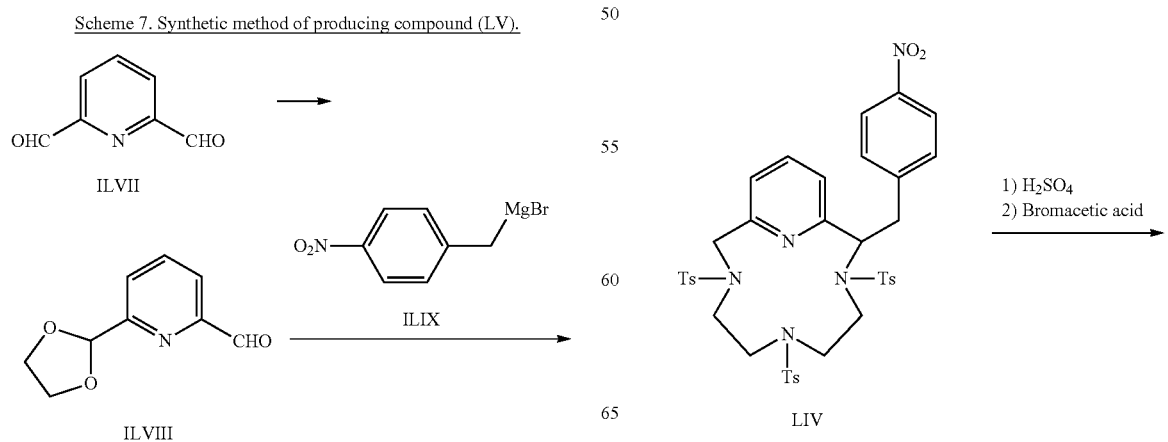

Scheme 7. Synthetic method of producing compound (LV).

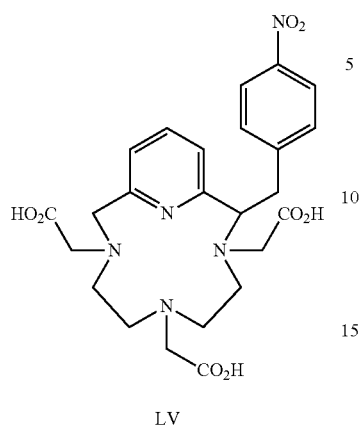

LV

Scheme 8 illustrates an example of a method that can be used to produce a compound of formula (XVIa). The compound 2,2'-oxydiacetaldehyde (LVI) is monoprotected to form the mono-acetal 24(1,3-dioxolan-2-yl)methoxy)acetaldehyde (LVII). Reaction of (LVII) with the Grignard reagent (4-nitrobenzyl)magnesium bromide (ILIX) produces the alcohol 1-((1,3-dioxolan-2-yl)methoxy)-3-(4-nitrophenyl) propan-2-ol (LVIII). The alcohol (LVIII) is deprotected with HCl, and the resulting aldehyde is reduced using NaBH$_4$ to produce the diol 1-(2-hydroxyethoxy)-3-(4-nitrophenyl)propan-2-ol (LVIX). Chlorination of (LVIX) with thionyl chloride yields the compound 1-(2-chloro-3-(2-chloroethoxy) propyl)-4-nitrobenzene (LVX). Cyclization of (LVX) with (LIII) results in the product 3-(4-nitrobenzyl)-4,7,10-tritosyl-1-oxa-4,7,10-triazacyclododecane (LVXI). Finally, deprotection of (LVXI) and alkylation with bromoacetic acid produces the compound 2,2',2''-(3-(4-nitrobenzyl)-1-oxa-4,7,10-triazacyclododecane-4,7,10-triyl)triacetic acid (LVXII). The nitro group of the compound (LVXII) can be converted to corresponding amino and isothiocyante derivatives according to the same methods outlined above.

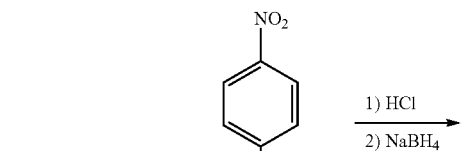

LVIII

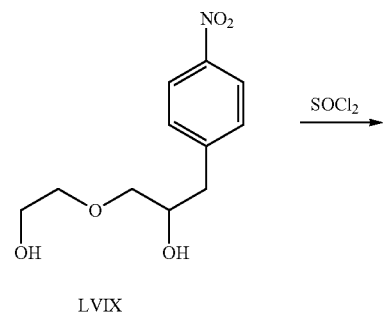

LVIX

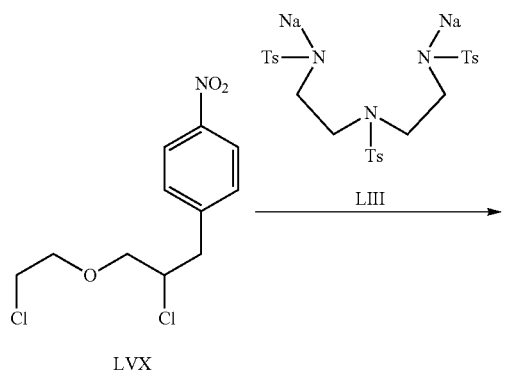

LVX

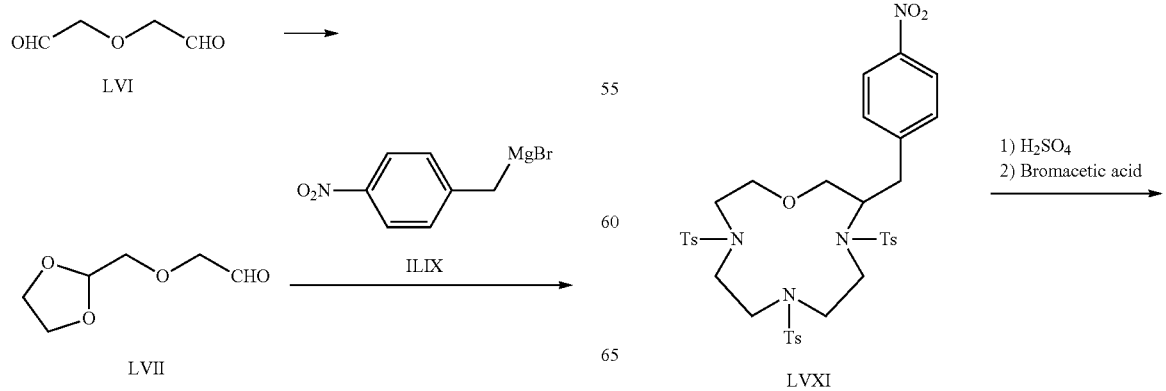

Scheme 8. Synthetic method of producing compound (LVXII).

LVI

LVII

LVXI

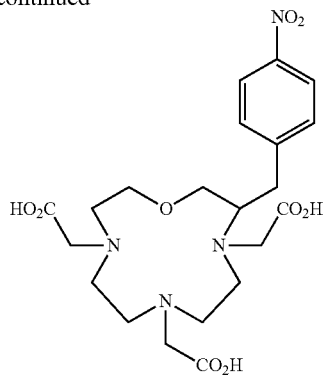

LVXII

Although the synthetic schemes described above relate to the production of racemic ligands or chelators, it is to be understood that these schemes can be easily modified to produce enantiomerically pure or enantiomerically enriched ligands having the (L) or (D)-configuration by using enantiomerically pure or enantiomerically enriched starting materials, or by including one or more resolution steps within these schemes, which are generally known in the art.

As used herein, the terms "degree of complexation" and "percent complexation" are used interchangeably and are defined to mean the percentage of the ion that is successfully complexed with the bifunctional chelant divided by the total ion used in the complexation reaction. The value of percent complexation obtained when making the ion complexes of the present reaction can be greater than 90% or greater than 95%, as measured by cation exchange.

The conjugates of the present invention can be prepared by first forming the complex and then attaching to the biological carrier. Thus, the process involves preparing or obtaining the ligand, forming the complex with an ion and then adding the biological carrier. Alternatively, the process may involve first conjugation of the ligand to the biological carrier and then the formation of the complex with an ion. Any suitable process that results in the formation of the ion-conjugates of this invention is within the scope of the present invention.

The complexes, bifunctional chelates and conjugates of the present invention are useful as diagnostic agents in the manner described. These formulations may be in kit form such that the two components (i.e., ligand and metal, complex and antibody, or ligand/antibody and metal) are mixed at the appropriate time prior to use. Whether premixed or as a kit, the formulations usually require a pharmaceutically acceptable carrier.

Tissue specificity may also be realized by ionic or covalent attachment of the chelate of formula (I) (where $R^1$ is $NH_2$, isothiocyanate, semicarbazido, thiosemicarbazido, maleimido, bromoacetamido or carboxyl group) to a naturally occurring or synthetic molecule having specificity for a desired target tissue. One possible application of this approach is through the use of chelate conjugated monoclonal antibodies which would transport the chelate to diseased tissue enabling visualization. The surgeon could then illuminate soft tissue with a UV light source coupled with an appropriate detector, if necessary, and surgically remove the indicated tissue.

The following examples are provided to further illustrate the present invention, and should not be construed as limiting thereof.

Materials

The compounds 2,2',2"-((4S)-4-(4-nitrobenzyl)-3,6,9,15-tetraazabicyclo[9.3.1]pentadeca-1(15),11,13-triene-3,6,9-triyl)triacetic acid [(L)-p-$NO_2$-Bz-PCTA]; and 2,2',2"-((4S)-4-(4-isothiocyanatobenzyl)-3,6,9,15-tetraazabicyclo[9.3.1]pentadeca-1(15),11,13-triene-3,6,9-triyl)triacetic acid [(L)-p-NCS-Bz-PCTA] were prepared according to the method outlined in Scheme 1 starting from (S)-$N^1$-(2-aminoethyl)-3-(4-nitrophenyl)propane-1,2-diamine. 2,2',2"-((4R)-4-(4-nitrobenzyl)-3,6,9,15-tetraazabicyclo[9.3.1]pentadeca-1(15),11,13-triene-3,6,9-triyl)triacetic acid [(D)-p-$NO_2$-Bz-PCTA] was prepared according to the method outlined in Scheme 1 starting from (R)—$N^1$-(2-aminoethyl)-3-(4-nitrophenyl)propane-1,2-diamine.

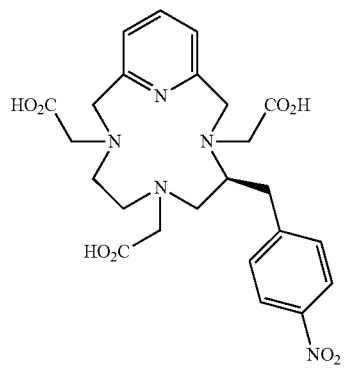

(L)-p-$NO_2$-Bz-PCTA

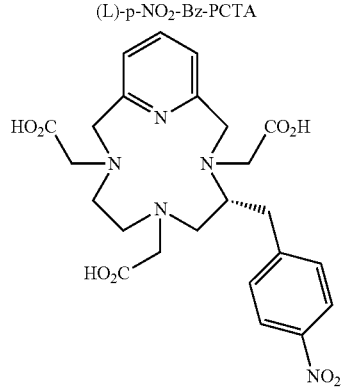

(D)-p-$NO_2$-Bz-PCTA

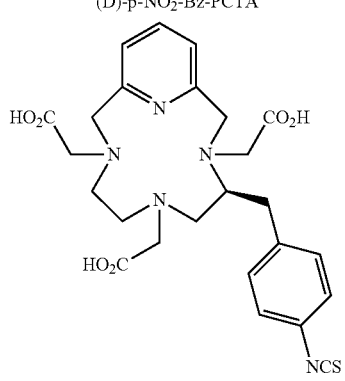

(L)-p-NCS-Bz-PCTA 2,2',2",2'''-(2-(4-nitrobenzyl)-1,4,7,10-tetraazacyclododecane-1,4,7,10-tetrayl)tetraacetic acid [(±)-p-$NO_2$-Bz-DOTA] and 2,2',2"-(1-oxa-4,7,10-triazacyclododecane-4,7,10-triyl)triacetic acid [(±)-OXO] were supplied by Macrocyclics, Inc. (Dallas, Tx). 2,2'-(6-(carboxy(2-methoxy-5-nitrophenyl)methyl)-3,6,9,15-tetraazabicyclo[9.3.1]

pentadeca-1(15),11,13-triene-3,9-diyl)diacetic acid [(±)-NPCTA] was prepared according to the method provided in U.S. Pat. No. 5,480,990, the disclosure of which is incorporated by reference herein.

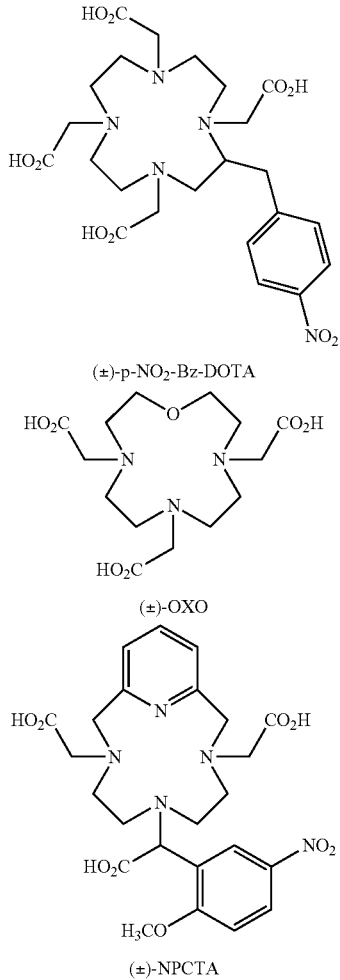

(±)-p-NO₂-Bz-DOTA (±)-OXO (±)-NPCTA

The compounds (S)-2,2',2''-(5-(4-nitrobenzyl)-1-oxa-4,7,10-triazacyclododecane-4,7,10-triyl)triacetic acid [(L)-p-NO₂-Bz-OXO] and (R)-2,2',2''-(5-(4-nitrobenzyl)-1-oxa-4,7,10-triazacyclododecane-4,7,10-triyl)triacetic acid [(D)-p-NO₂-Bz-OXO] 3 were prepared according to the method outlined in Scheme 3 starting from (S)-N¹-(2-aminoethyl)-3-(4-nitrophenyl)propane-1,2-diamine and (R)-N¹-(2-aminoethyl)-3-(4-nitrophenyl)propane-1,2-diamine, respectively.

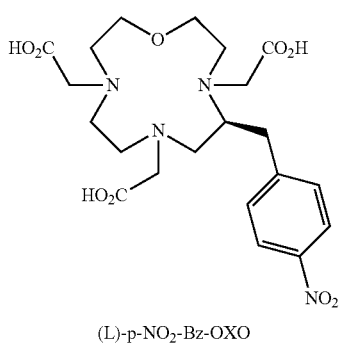

(L)-p-NO₂-Bz-OXO

-continued

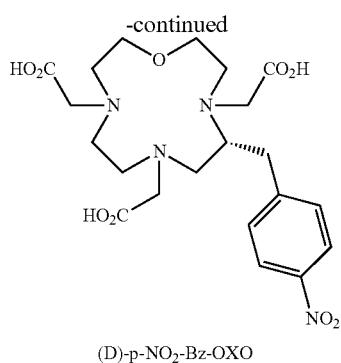

(D)-p-NO₂-Bz-OXO

Complexation Studies.
General

A polyazamacrocyclic ligand ((L)-p-NO₂-Bz-PCTA; (D)-p-NO₂-Bz-PCTA; (L)-p-NCS-Bz-PCTA; (±)-p-NO₂-Bz-DOTA, (±)-NPCTA, (±)-OXO and (L)-p-NO₂-Bz-OXO) was combined with a metal ion ($^{90}Y^{3+}$, $^{111}In^{3+}$, $^{177}Lu^{3+}$) at room temperature in buffer at a molar ratio of the ligand to the metal ion of 100:1 for kinetic studies, 200:1 for stability studies or at values ranging from 2:1 to 200:1 for the molar ratio studies.

Complexation studies involving $^{90}Y^{3+}$ and $^{111}In^{3+}$ were conducted with 50-100 mM sodium acetate buffer, pH 5.0-7.0, while complexation studies involving $^{177}Lu^{3+}$ were performed with 50 mM-100 mM sodium acetate buffer, pH 4-5.

In the stability studies, 100 μL of a solution containing a complex of a ligand with a metal ion was mixed with 500 μL of serum, or 0.1 M Glycine buffer at pH=2, 4 or 6

1 μL samples were taken at 10 minute intervals for kinetic studies, after 60 minutes in experiments studying the effect of the value of [ligand]/[metal ion] on the % complexation of the ligand, and at spaced intervals of 1-3 days for experiments studying the stability of complexes formed using the ligand of the present invention. Following the method generally described by SARA (Fundamentals of Nuclear Pharmacy, Springer, 4$^{th}$ edition, pages 151-158, the disclosure of which is incorporated herein by reference), the free metal and labeled chelate are separated by thin layer chromatography using silica gel paper (1 cm×6 cm) and a mobile phase (acetone:saline v/v=1:1). The silica gel paper is cut in half and each half is measured in a gamma well counter. The results of the kinetic studies are illustrated in FIGS. 1-3, the results of the experiments studying the effect of [ligand]/[metal ion] on the % complexation of the ligand are shown in FIGS. 4-6, and the results of the stability studies are illustrated in FIGS. 7-9. Each result shown in FIGS. 4-9 is the average of three separate trials.

EXAMPLE 1

Kinetics of Complexation of Polyazamacrocyclic Ligand with Metal Ion

A) Complexation Studies Involving $^{90}Y^{3+}$

The fastest initial rate of complexation was observed with (L)-p-NO₂-Bz-PCTA (95% complexation after 10 minutes), followed succesively by (±)-p-NO₂-Bz-DOTA, (±)-OXO, (D)-p-NO₂-Bz-PCTA, (L)-p-NCS-Bz-PCTA, (L)-p-NO₂-Bz-OXO and (±)-NPCTA. For (±)-p-NO₂-Bz-DOTA, (±)-OXO and (L)-p-NO₂-Bz-OXO, values of percent complexation above 95% were achieved after 30 minutes. In general, the highest percent complexation of metal ion was observed with the ligands (L)-p-NO$_2$-Bz-PCTA, (±)-p-NO$_2$-Bz-DOTA, (±)-OXO and (L)-p-NO$_2$-Bz-OXO.

The relatively slower kinetics of complexation associated with (±)-NPCTA may be attributed to a steric or electronic effect associated with the position of the pendant linker p-NO$_2$-Bz group on the macrocyclic ring.

B) Complexation Studies Involving $^{111}$In$^{3+}$

The fastest initial rate of complexation was observed with (±)-OXO, (L)-p-NO$_2$-Bz-OXO and (L)-NCS-Bz-PCTA (each having a value of percent complxation of greater than 95% after 10 minutes, followed successively by (L)-p-NO$_2$-Bz-PCTA (~95% complexation after 10 minutes), (D)-p-NO$_2$-Bz-PCTA, (±)-p-NO$_2$-Bz-DOTA and (±)-NPCTA.

The highest percent complexation of metal ion was observed with the ligands (±)-OXO, (L)-p-NO$_2$-Bz-OXO, (±)-NCS-Bz-PCTA and (L)-p-NO$_2$-Bz-PCTA, which had maximum values of complexation of greater than 95%. (±)-p-NO$_2$-Bz-DOTA displayed a maximum values of complexation of ~89% after 40 minutes.

The relatively slower kinetics of complexation associated with (±)-NPCTA may be attributed to a steric or electronic effect associated with the position of the pendant linker p-NO$_2$-Bz group on the macrocyclic ring.

C) Complexation Studies Involving $^{177}$Lu$^{3+}$

The fastest initial rate of complexation was observed with (L)-p-NO$_2$-Bz-PCTA and (L)-p-NO$_2$-Bz-OXO (>95% complexation after 10 minutes) followed successively by (±)-OXO, (±)-p-NO$_2$-Bz-DOTA, (D)-p-NO$_2$-Bz-PCTA, (±)-NPCTA and (L)-p-NCS-Bz-PCTA. (±)-OXO and (±)-p-NO$_2$-Bz-DOTA each displayed ~95% complexation after 10 minutes, while (D)-p-NO$_2$-Bz-PCTA showed only ~91% complexation after 10 minutes. With (±)-p-NO$_2$-Bz-DOTA and (±)-NPCTA, the maximum percent of complexation was observed only after 40 minutes and 50 minutes, respectively.

In general, the highest percent complexation of metal ion was observed with the ligands (L)-p-NO$_2$-Bz-PCTA, (L)-p-NO$_2$-Bz-OXO, (±)-OXO, and (±)-p-NO$_2$-Bz-DOTA.

The relatively slower kinetics of complexation associated with (±)-NPCTA may be attributed to a steric or electronic effect associated with the position of the pendant linker p-NO$_2$-Bz group on the macrocyclic ring.

EXAMPLE 2

Effect of [Ligand]/[Metal Ion] on the Percent Complexation of the Ligand

A) Effect of [ligand]/[$^{90}$Y$^{3+}$] on the Percent Complexation of the Ligand A value of percent complexation of above 95% was achieved with (±)-p-NO$_2$-Bz-DOTA and (L)-p-NO$_2$-Bz-PCTA at a molar ratio of ligand/$^{90}$Y$^{3+}$ of 2:1. With (D)-p-NO$_2$-Bz-PCTA, ~95% complexation was achieved at a molar ratio of ligand/$^{90}$Y$^{3+}$ of 10:1. For (±)-OXO and (L)-p-NO$_2$-Bz-PCTA, a value of above 95% complexation was obtained at the molar ratio of ligand/$^{90}$Y$^{3+}$ of 5:1 or above. A value of 90% complexation was not achieved with (±)-NPCTA even at values of molar ratio of ligand/$^{90}$Y$^{3+}$ of greater than 20:1.

B) Effect of [ligand]/[$^{111}$In$^{3+}$] on the percent complexation of the ligand A value of percent complexation of above 95% was achieved with (L)-p-NO$_2$-Bz-PCTA and with (L)-p-NO$_2$-Bz-OXO, at a molar ratio of ligand/$^{111}$In$^{3+}$ of 2:1. With (D)-p-NO$_2$-Bz-PCTA, ~95% complexation was achieved at a molar ratio of ligand/$^{111}$In$^{3+}$ of 10:1. With (±)-p-NO$_2$-Bz-DOTA, ~94% complexation was achieved at a molar ratio of ligand/$^{111}$In$^{3+}$ of 5:1. A value of percent complexation of above 95%, however, was not achieved with (±)-p-NO$_2$-Bz-DOTA even at a molar ratio of ligand/$^{111}$In$^{3+}$ of greater than 20:1. For (±)-OXO, a value of above 95% complexation was obtained at a molar ratio of ligand/$^{111}$In$^{3+}$ of 5:1 or above. A value of ~76% complexation was achieved with (±)-NPCTA at a molar ratio of ligand/$^{111}$In$^{3+}$ of 5:1.

C) Effect of [Ligand]/[$^{177}$Lu$^{3+}$] on the % Complexation of the Ligand

A value of greater than 95% complexation was achieved with (L)-p-NO$_2$-Bz-OXO at values of molar ratio of ligand/$^{177}$Lu$^{3+}$ of 2:1 and above. With (L)-p-NO$_2$-Bz-PCTA, a value of percent complexation of ~95% was achieved with (L)-p-NO$_2$-Bz-PCTA at a molar ratio of ligand/$^{177}$Lu$^{3+}$ of 5:1. With (D)-p-NO$_2$-Bz-PCTA, greater than 95% complexation was achieved at a molar ratio of ligand/$^{177}$Lu$^{3+}$ of 5:1. With (±)-p-NO$_2$-Bz-DOTA, greater than 95% complexation was only achieved at a molar ratio of ligand/$^{177}$Lu$^{3+}$ of 100:1. For (±)-OXO, a value of above 95% complexation was obtained at the molar ratio of ligand/$^{177}$Lu$^{3+}$ of 10:1 or above. A value of ~95% complexation was not achieved with (±)-NPCTA even at values of molar ratio of ligand/$^{177}$Lu$^{3+}$ of greater than 20:1.

EXAMPLE 3

Stability Studies

FIGS. 7-9 illustrate the stability of (±)-p-NO$_2$-Bz-DOTA-metal ion complex and a (L)-p-NO$_2$-Bz-PCTA-metal ion complex in serum, or 0.1 M Glycine buffer (pH=2, 4 or 6) as a function of time, where the metal ion is $^{90}$Y$^{3+}$, $^{111}$In$^{3+}$ or $^{177}$Lu$^{3+}$.

(L)-p-NO$_2$-Bz-PCTA-$^{90}$Y$^{3+}$ complex was relatively more stable than the (±)-p-NO$_2$-Bz-DOTA-$^{90}$Y$^{3+}$ complex in serum. The stability of the two complexes were similar in Glycine buffer, pH 2, 4 or 5.

Both the (L)-p-NO$_2$-Bz-PCTA-$^{111}$In$^{3+}$ complex and the (±)-p-NO$_2$-Bz-DOTA-$^{111}$In$^{3+}$ complex were similarly stable in 0.1 M Glycine buffer, pH 2, 4 or 5. The (L)-p-NO$_2$-Bz-PCTA-$^{111}$In$^{3+}$ complex was relatively more stable than the (±)-p-NO$_2$-Bz-DOTA-$^{111}$In$^{3+}$ complex in serum over time.

Both the (L)-p-NO$_2$-Bz-PCTA-$^{177}$Lu$^{3+}$ complex and the (±)-p-NO$_2$-Bz-DOTA-$^{177}$Lu$^{3+}$ complex were relatively less stable in serum compared to 0.1 M Glycine buffer, pH 2, 4 or 5. The (±)-p-NO$_2$-Bz-DOTA-$^{177}$Lu$^{3+}$ complex was relatively more stable than the (L)-p-NO$_2$-Bz-PCTA-$^{177}$Lu$^{3+}$ complex in each one of 0.1 M Glycine buffer, pH 2, 4 or 5.

The present invention has been described with regard to one or more embodiments. However, it will be apparent to persons skilled in the art that a number of variations and modifications can be made without departing from the scope of the invention as defined in the claims.

All citations are hereby incorporated by reference.

References (1) Mark Woods, Z. K., A. Dean Sherry Journal of Suprmolecular Chemistry 2002, 2, 1-15.
(2) Wynn A. Volkert, a. T. J. H. Chem. Rev. 1999, 99, 2269-2292.
(3) Peter Caravan, J. J. E., Thomas J. McMurry, and Randall B. Lauffer Chem. Rev. 1999, 99, 2293-2352.
(4) G. M. Lanza, R. L., S. Caruthers, S. A. Wickline MEDICAMUNDI 2003, 47, 34-39.
(5) Edwards, S. L. a. D. S. Bioconjugate Chemistry 2001, 12, 7-34.
(6) Paul A. Whetstone, N. G. B., Todd M. Corneillie, and Claude F. Meares Bioconjugate Chemistry 2004, 15, 3-6.

(7) Julie B. Stimmel, M. E. S., and Frederick C. Kull, Jr. Bioconjugate Chemistry 1995, 6, 219-225.
(8) Hyun-soon Chong, K. G., Dangshe Ma, Diane E. Milenic, Terrish Overstreet, and; Brechbiel, M. W. J. Med. Chem. 2002, 45, 3458-3464.

The invention claimed is:

1. A bifunctional polyazamacrocyclic chelating agent of the formula (VIb) or (VIe):

(VIb)

(VIe)

wherein:
each Q is independently $(CHR^5)_p CO_2 R$ or $(CHR^5)_p PO_3 R^6 R^7$;
$Q^1$ is hydrogen, $(CHR^5)_w CO_2 R$ or $(CHR^5)_w PO_3 R^6 R^7$;
each R is independently hydrogen, benzyl or $C_1$-$C_4$ alkyl;
$R^6$ and $R^7$ are independently H, $C_1$-$C_6$ alkyl or ($C_1$-$C_2$ alkyl) phenyl;
each $R^5$ is independently hydrogen; $C_1$-$C_4$ alkyl or ($C_1$-$C_2$ alkyl) phenyl;
A is CH, N, C—Br, C—Cl, C—$SO_3H$, C—$OR^8$, C—$OR_9$, $N^+$—$R^{10}X^-$, or C—C≡C—⟨phenyl⟩—$R^{11}$;

Z and $Z^1$ independently are CH, N, C—$SO_3H$, $N^+$—$R^{10}X^-$, C—$CH_2$—$OR^8$ or C—C(O)—$R^{11}$;
$R^8$ is H, $C^1$-$C^5$ alkyl, benzyl, or benzyl substituted with at least one $R^{12}$;
$R^9$ is $C^1$-$C_{16}$ alkylamino;
$R^{10}$ is $C_1$-$C_{16}$ alkyl, benzyl, or benzyl substituted with at least one $R^{12}$;
$R^{11}$ is —O—($C_1$-$C_3$ alkyl), OH or NHR—;
$R^{12}$ is H, $NO_2$, $NH_2$, isothiocyanato, semicarbazido, thiosemicarbazido, maleimido, bromoacetamido or carboxyl;
X and Y are each independently hydrogen or may be taken with an adjacent X and Y to form an additional carbon-carbon bond;
n is 0 or 1;
m is an integer from 0 to 10 inclusive;
p is 1 or 2;
r is 0 or 1;
w is 0 or 1;
L is a linker/spacer group covalently bonded to, and replaces one hydrogen atom of one of the carbon atoms to which it is joined, said linker/spacer group being represented by the formula:

wherein:
s is 1;
t is an integer from 0 to 20 inclusive;
$R^1$ is an electrophilic or nucleophilic moiety which allows for covalent attachment to a biological carrier, or synthetic linker which can be attached to a biological carrier, or precursor thereof; and
Cyc represents a cyclic aliphatic moiety, aromatic moiety, aliphatic heterocyclic moiety, or aromatic heterocyclic moiety, each of said moieties optionally substituted with one or more groups which do not interfere with binding to a biological carrier;
or a pharmaceutically acceptable salt thereof.

2. The bifunctional polyazamacrocyclic chelating agent according to claim 1, wherein the chelating agent is of the formula (VIIb):

(VIIb)

3. The bifunctional polyazamacrocyclic chelating agent according to claim 2, wherein Q is $(CHR^5)_p CO_2 R$.

4. The bifunctional polyazamacrocyclic chelating agent according to claim 2, wherein the chelating agent is of the formula (VIIIb):

(VIIIb)

5. The bifunctional polyazamacrocyclic chelating agent according to claim 4, wherein the chelating agent is of the formula (IXb):

(IXb)

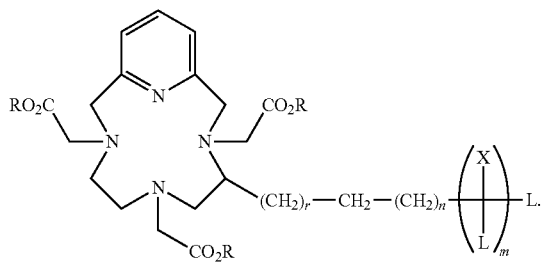

6. The bifunctional polyazamacrocyclic chelating agent according to claim 5, wherein the chelating agent is of the formula (Xb):

(Xb)

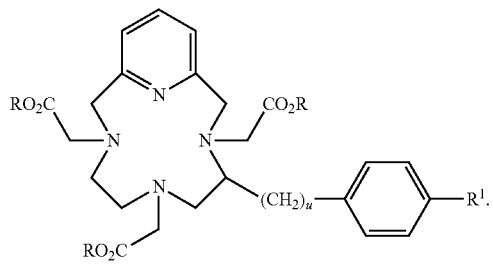

wherein u is 1, 2, 3, 4 or 5.

7. The bifunctional polyazamacrocyclic chelating agent according to claim 6, wherein the chelating agent is of the formula (XIb):

(XIb)

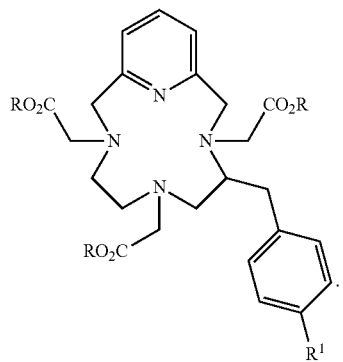

8. A complex comprising a bifunctional polyazamacrocyclic chelating and an ion of a stable or radioactive metal selected from the group consisting of La, Sm, Eu, Gd, Tb, Dy, Ho, Er, Tm, Yb, Lu, Y, Cr, Cu, Pt, Re, Tc, Fe, Mg, Mn and Sc, wherein the bifunctional polyazamacrocyclic chelating agent is of the formula (I):

(I)

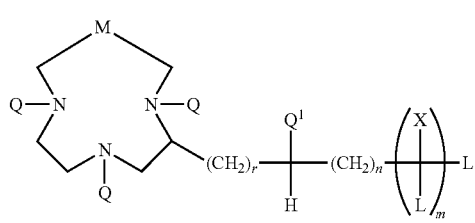

wherein:

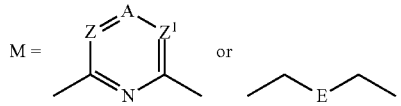

each Q is independently $(CHR^5)_p CO_2 R$ or $(CHR^5)_p PO_3 R^6 R^7$;
$Q^1$ is hydrogen, $(CHR^5)_w CO_2 R$ or $(CHR^5)_w PO_3 R^6 R^7$;
each R is independently hydrogen, benzyl or $C_1$-$C_4$ alkyl;
$R^6$ and $R^7$ are independently H, $C_1$-$C_6$ alkyl or ($C_1$-$C_2$ alkyl)phenyl;
each $R^5$ is independently hydrogen; $C_1$-$C_4$ alkyl or ($C_1$-$C_2$ alkyl)phenyl;
A is CH, N, C—Br, C—Cl, C—$SO_3$H, C—$OR^8$, C—$OR_9$, $N^+$—$R^{10}X^-$, or

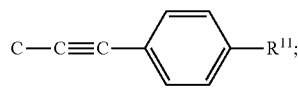

Z and $Z^1$ independently are CH, N, C—$SO_3$H, $N^+$—$R^{10}X^-$, C—$CH_2$—$OR^8$ or C—C(O)—$R^{11}$;
E is O, S or P;
$R^8$ is H, $C^1$-$C^5$ alkyl, benzyl, or benzyl substituted with at least one $R^{12}$;
$R^9$ is $C_1$-$C_{16}$ alkylamino;
$R^{10}$ is $C_1$-$C_{16}$ alkyl, benzyl, or benzyl substituted with at least one $R^{12}$;
$R^{11}$ is —O—($C_1$-$C_3$ alkyl), OH or NHR—;
$R^{12}$ is H, $NO_2$, $NH_2$, isothiocyanato, semicarbazido, thiosemicarbazido, maleimido, bromoacetamido or carboxyl;
X and Y are each independently hydrogen or may be taken with an adjacent X and Y to form an additional carbon-carbon bond;
n is 0 or 1;
m is an integer from 0 to 10 inclusive;
p is 1 or 2;
r is 0 or 1;
w is 0 or 1;
L is a linker/spacer group covalently bonded to, and replaces one hydrogen atom of one of the carbon atoms to which it is joined, said linker/spacer group being represented by the formula:

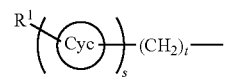

wherein:
s is an integer of 1;
t is an integer of 0 to 20 inclusive;
$R^1$ is an electrophilic or nucleophilic moiety which allows for covalent attachment to a biological carrier, or synthetic linker which can be attached to a biological carrier, or precursor thereof; and
Cyc represents a cyclic aliphatic moiety, aromatic moiety, aliphatic heterocyclic moiety, or aromatic heterocyclic moiety, each of said moieties optionally substituted with one or more groups which do not interfere with binding to a biological carrier;
or a pharmaceutically acceptable salt thereof.

9. A conjugate comprising the complex of claim 8 covalently attached to a biological carrier.

10. The conjugate according to claim 9, wherein the biological carrier is a protein, antibody, antibody fragment, hormone, peptide, growth factor, antigen or hapten.

11. A complex comprising the bifunctional polyazamacrocyclic chelating agent as defined in claim 8, and an ion of a metal selected from the group consisting of $^{90}$Y, $^{177}$Lu, $^{111}$In, $^{64}$Cu, $^{67}$Cu, $^{153}$Sm, $^{153}$Gd, $^{159}$Gd, $^{166}$Ho, $^{149}$Pm, $^{175}$Yb, $^{47}$Sc, $^{142}$Pr, $^{99m}$Tc, $^{188}$Re, $^{186}$Re, $^{67}$Ga, $^{68}$Ga, $^{89}$Zr, and $^{212}$Bi.

12. A conjugate comprising the complex of claim 11 covalently attached to a biological carrier.

13. The conjugate according to claim 12, wherein the biological carrier is a protein, antibody, antibody fragment, hormone, peptide, growth factor, antigen or hapten.

14. A pharmaceutical composition comprising the conjugate of claim 9, and a pharmaceutically acceptable carrier.

15. A pharmaceutical formulation comprising the conjugate of claim 12, and a pharmaceutically acceptable carrier.

* * * * *